US007956193B2

(12) United States Patent
Zhang et al.

(10) Patent No.: US 7,956,193 B2
(45) Date of Patent: Jun. 7, 2011

(54) INTRAMOLECULAR C-H AMINATION WITH SULFONYL AZIDES

(75) Inventors: X. Peter Zhang, Tampa, FL (US); Joshua V. Ruppel, Lutz, FL (US)

(73) Assignee: University of South Florida, Tampa, FL (US)

( * ) Notice: Subject to any disclaimer, the term of this patent is extended or adjusted under 35 U.S.C. 154(b) by 361 days.

(21) Appl. No.: 12/151,182

(22) Filed: May 5, 2008

(65) Prior Publication Data

US 2010/0063277 A1   Mar. 11, 2010

Related U.S. Application Data

(60) Provisional application No. 60/916,071, filed on May 4, 2007.

(51) Int. Cl.
*C07D 513/00* (2006.01)
*C07D 279/02* (2006.01)
*C07D 275/02* (2006.01)
*C07D 275/04* (2006.01)

(52) U.S. Cl. ........................................ 548/207; 540/145
(58) Field of Classification Search .................. 548/207; 540/145
See application file for complete search history.

(56) References Cited

U.S. PATENT DOCUMENTS

| 6,353,112 | B1 | 3/2002 | Baker et al. |
| 6,365,612 | B2 | 4/2002 | Genin et al. |
| 6,458,962 | B1 | 10/2002 | Mao et al. |
| 6,562,850 | B1 | 5/2003 | Baker et al. |
| 6,951,935 | B2 | 10/2005 | Zhang et al. |
| 2005/0124596 | A1 | 6/2005 | Zhang et al. |
| 2006/0030718 | A1 | 2/2006 | Zhang et al. |

OTHER PUBLICATIONS

Abramovitch et al., J. Org. Chem., 1977, 2920-2926, 42 (17).
Dauban et al., Synlett 2003, 1571-1586, No. 11.
Elgazwy, Tetrahedron 2003, 7445-7463, 59.
Espino et al., J. Am. Chem. Soc. 2001, 6935-6936, 123 (28).
Espino et al., Modern Rhodium-Catalyzed Organic Reactions, 2005, 379-416, Wiley-VCH, Weinheim.
Hansch et al., J. Org. Chem., 1956, 265-270, 21 (3).
Headrick, Dissertation 2003, University of Tennessee, Knoxville.
Rapoport et al., J. Org. Chem. 1988, 2367-2371, 53.
Ruppel et al., Organic Letters 2007, 4889-4892, 9 (23).
Zaharevitz et al., Med. Chem. Res. 1999, 551-564, 9.
Abdel-Sattar et al., Tetrahedron, 59, 7445-7463, 2003.
Albone et al., J. Org. Chem., 63, 9569-9571, 1998.
Antunes et al., Chem. Commun, 405-406, 2001.
Brase et al., Angew Chem. Int. Ed., 44, 5188-5240, 2005.
Cenini, et al., Chem. Commun. 2265-2266, 2000.
Cenini et al., Coor. Chem. Rev., 250, 1234-1253, 2006.
Chanda et al., J. Org. Chem., 66, 30-34, 2001.
Chen et al., JACS, 126, 14718-14719, 2004.
Chen et al., J. Org. Chem., 69, 2431-2435, 2004.
Chen et al., Tetrahedron Ltrs., 46, 4965-4969, 2005.
Cui, Angew Chem. Int., 43, 4210-4112, 2004.
Davies et al., Angew, 44 3518-3520, 2005.
Davies, Angew Chem. Int. Ed., 45 6422-6425, 2006.
Dauban et al., JACS, 123, 7707-7708, 2001.
Espino et al., Angew Chem. Int. Ed., 40, 598-600, 2001.
Gao et al., Org. Ltrs., 7, 3191-3193, 2005.
Gao, et al., J. Org. Chem., 71, 6655-6658, 2006.
Guthikonda et al., Jacs, 124, 13672-13673, 2002.
Halfen, Current Org. Chem., 9, 657-669, 2005.
Han et al., Tetrahedron Ltrs., 47, 7225-7228, 2006.
Huang et al., J. Org. Chem., 68, 8179-8184, 2003.
Katsuki et al., Chem. Ltrs., 34, 1304-1309, 2005.
Kawabata et al., Chem. Asian J., 2, 248-256, 2007.
Koser et al., Topics Current Chem., 224, 137-172, 2003.
Lebel et al., JACS, 127, 14198-14199, 2005.
Lebel et al., Pure Appl. Chem., 78, 363-375, 2006.
Lebel et al., Org. Ltrs., 9, 639-642, 2007.
Lee et al., Organometallics, 22, 4905-4909, 2003.
Lee et al., Curr. Org. Chem., 11, 213-228, 2007.
Liang et al., Angew Chem. Int.Liang, Angew Chem. Int., 45, 4641-4644, 2006, 45, 4641-4644, 2006.
Liu, et al., Heterocycles, vol. 56, 693-709, 2002.
Muller et al., Chem. Rev., 103, 2905-2919, 2003.
Omura et al., Chem. Ltrs., 32, 354-355, 2003.
Omura et al., Chem. Comm., 2060-2061, 2004.
Piangiolino et al., Eur. J. Org. Chem., 743-750, (2007).
Ragaini et al., Chem. Eur. J., 9, 249, 2003.
Reddy et al., Org. Ltrs., 8, 5013-5016, 2006.
Scriven et al., Chem. Rev., 88, 297-368, 1988.
Simkhovich et al., Tetrahedron Ltrs., 42, 8089-8092, 2001.
Vyas et al., Org. Ltrs., 6, 1907-1910, 2004.
Yu et al., Organic Ltrs., 2, 2233-2236, 2000.

*Primary Examiner* — Kahsay T Habte
(74) *Attorney, Agent, or Firm* — Bryan Cove LLP

(57) ABSTRACT

Cobalt (II) complexes of porphyrins are effective catalysts for intramolecular nitrene insertion of C—H bonds with arylsulfonyl azides. The cobalt-catalyzed process can proceed efficiently under mild and neutral conditions in low catalyst loading without the need of other reagents or additives, generating nitrogen gas as the only byproduct. Using the simple tetraphenylporphyrin (TPP) as the ligand, the cobalt-catalyzed intramolecular amidation can be applied to primary, secondary, and tertiary C—H bonds and suitable for a broad range of arylsulfonyl azides, leading to the syntheses of various benzosultam derivatives in excellent yields

32 Claims, 1 Drawing Sheet

INTRAMOLECULAR C-H AMINATION WITH SULFONYL AZIDES

CROSS-REFERENCE TO RELATED APPLICATIONS

This application claims priority to U.S. Provisional Application Ser. No. 60/916,071, filed May 4, 2007, which is incorporated herein by reference in its entirety.

STATEMENT OF GOVERNMENT RIGHTS

This invention was made with Government support under grant number NSF #0711024, awarded by the National Science Foundation, Division of Chemistry and the American Chemical Society, Petroleum Research Fund (PRF #44286-AC1). The Government has certain rights in the invention.

BACKGROUND

The present invention generally relates to an environmentally benign and economically attractive catalytic process that allows preparation of value-added nitrogen compounds from readily available hydrocarbons.

Metal-mediated nitrene transfer reactions are fundamentally and practically important chemical processes that allow selective conversion of readily available hydrocarbons to synthetically and biologically valuable nitrogen-containing compounds via direct C—N bond formation. Using [N-(p-toluenesulfonyl)imino]phenyl iodinane (PhI=NTs) and related iminoiodane derivatives as the primary nitrene sources, significant progress has been made in both catalytic aziridination of alkenes and amination of C—H bonds.

Several limitations have been noted, however, with the use of iminoiodanes: commercial unavailability, high costly synthesis, short shelf life, insolubility in common solvents, and the generation of ArI as by-products. While the approach of in situ generation of iminoiodanes in the presence of terminal oxidants has met with enormous successes recently, alternative nitrene sources such as chloramine-T, bromamine-T, and tosyloxycarbamates have been actively pursued to improve catalytic nitrene transfer reactions Azides represent a broad class of compounds that are considered ideal nitrene sources for metal-mediated nitrene transfer reactions. In addition to their wide availability and easy synthesis, azide-based nitrene transfers generate the chemically stable and environmentally benign nitrogen gas as the byproduct. Despite these advantages, only a few catalytic systems have been developed to catalyze the decomposition of azides for aziridination and amination effectively. Notable examples include Co(Por)-based amination with arylazides and Ru(Salen)-based aziridination with arylsulfonyl azides.

SUMMARY OF THE INVENTION

Among the various aspects of the present invention, therefore, may be noted the provision of a catalytic process for intramolecular C—H amination with azides, more specifically, intramolecular C—H amination with sulfonyl azides to produce sultams, and, in a preferred embodiment, a Co-based catalytic system for intramolecular C—H amination with benzosulfonyl azides, leading to the valuable benzosultam derivatives in excellent yields.

Briefly, therefore, the present invention is directed to a process for the for the preparation of a sultam. The process comprises treating a sulfonyl azide with a metal porphyrin complex to catalyze the amination of a C—H bond to form the sultam.

The present invention is further directed to a process for the intramolecular nitrene insertion of C-H bonds with arylsulfonyl azides with cobalt (II) complexes of porphyrins.

Other aspects of the invention will be in part apparent, and in part point out hereinafter.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENTS

Figure 1:
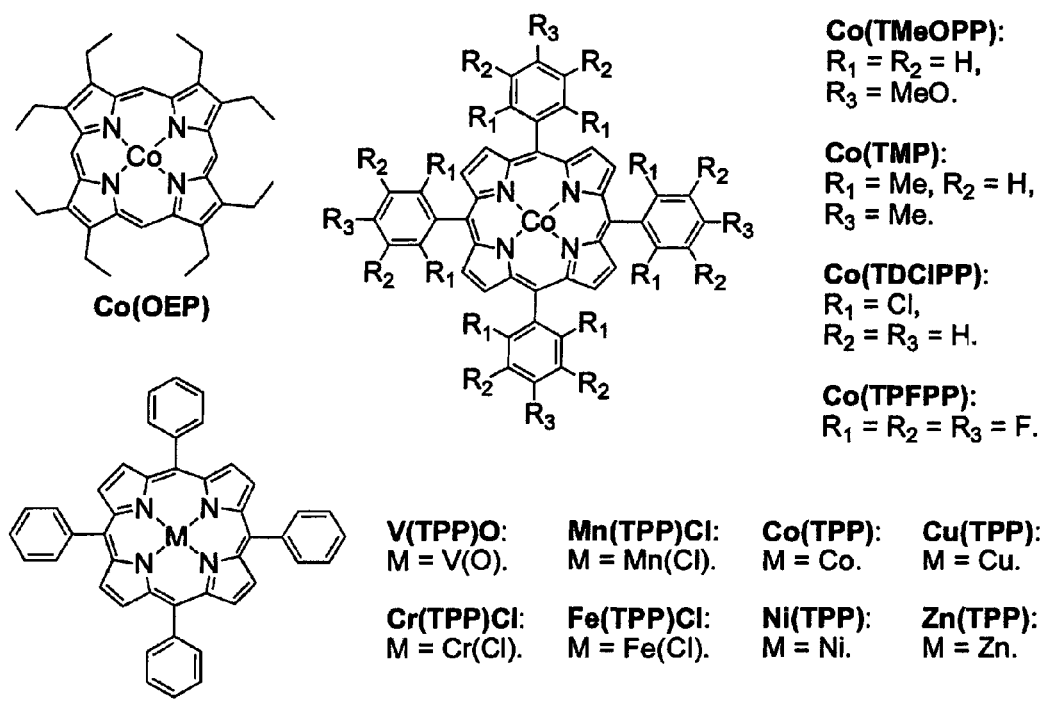
FIG. 1 shows structures of Cobalt (II) Complexes of Various Porphyrins.

In accordance with the process of the present invention, intramolecular nitrene insertion of C—H bonds with sulfonyl azides may be catalyzed with metal porphyrin complexes. The catalytic system can be applied to primary, secondary, and tertiary C—H bonds and is suitable for a broad range of sulfonyl azides, e.g., arylsulfonyl azides. In addition, the metal porphyrin catalyzed process advantageously proceeds relatively efficiently under relatively mild and neutral conditions in low catalyst loading without the need of other reagents or additives.

In accordance with a preferred embodiment, a sulfonyl azide 1 is converted to a sultam 2 as illustrated in Reaction Scheme 1:

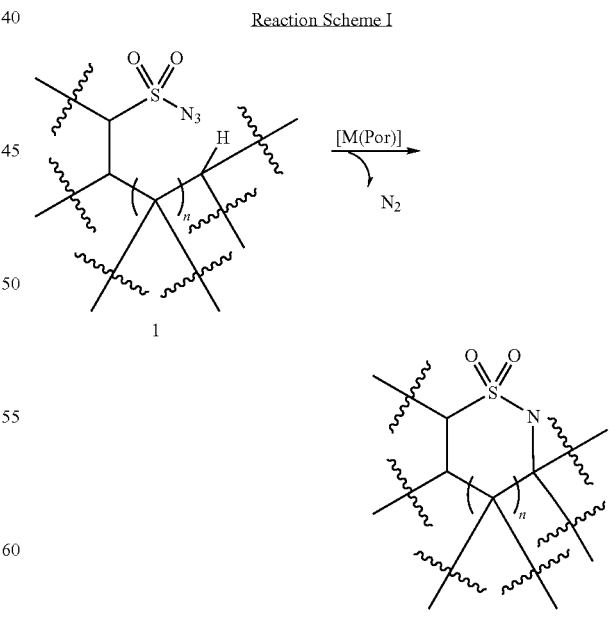

Reaction Scheme I wherein M(Por) is a metal porphyrin complex and n is 0 or 1.

Thus, for example, when n is 0, sultam 2 is a 5-membered ring corresponding to Formula 3 and when n is 1, sultam 2 is a 6-membered ring corresponding to Formula 4:

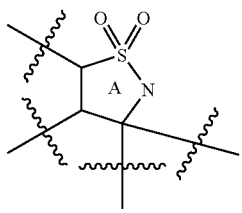

Formula 3

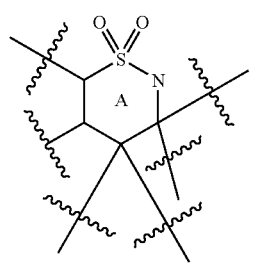

Formula 4

As depicted in Formulae 1, 2, 3, and 4, the metal porphyrin catalyzed intramolecular nitrene insertion of C—H bonds does not critically depend upon the substituents of the carbon atoms that are alpha, beta, gamma, or delta to the sulfonyl azide moiety and, as such, only the bonds to other (unidentified) atoms are depicted.

In one preferred embodiment, sultam 2 is a 5-membered or 6-membered ring, A, corresponding to Formula 5 or Formula 6, respectively:

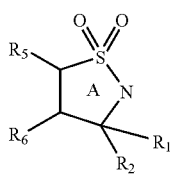

Formula 5

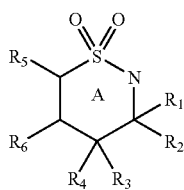

Formula 6 wherein $R_1$, $R_2$, $R_3$, and $R_4$ are independently hydrogen, hydrocarbyl, substituted hydrocarbyl, halo, hydroxyl, alkoxyl, or heterocyclo, and $R_5$ and $R_6$ are independently hydrogen, hydrocarbyl, substituted hydrocarbyl, halo, hydroxyl, alkoxyl, amino or heterocyclo or, in combination form a carbocyclic or heterocyclic ring fused to the A ring of the sultam of Formula 5 or Formula 6. In one embodiment, $R_1$, $R_2$, $R_3$, and $R_4$ are independently hydrogen, hydrocarbyl, substituted hydrocarbyl or heterocyclo. For example, $R_1$, $R_2$, $R_3$, and $R_4$ may be independently selected from hydrogen, alkyl, alkenyl, aryl and heterocyclo. In one embodiment, one of $R_1$ and $R_2$ is hydrogen and the other is hydrocarbyl, substituted hydrocarbyl, halo, hydroxyl, alkoxyl, or heterocycle; by way of example, in this embodiment, $R_1$ may be hydrogen and $R_2$ may be alkyl, aryl, or heterocycle (such as furyl). Similarly, in one embodiment, one of $R_3$ and $R_4$ is hydrogen and the other is hydrocarbyl, substituted hydrocarbyl, halo, hydroxyl, alkoxyl, or heterocycle; by way of example, in this embodiment, $R_3$ may be hydrogen and $R_4$ may be alkyl, aryl, or heterocycle (such as furyl). In another embodiment, the ring carbon atom to which $R_1$ and $R_2$ are attached is a Spiro atom and $R_1$, $R_2$, and the Spiro carbon atom to which they are attached, in combination, form a ring, typically containing three to seven ring atoms selected from carbon, oxygen, nitrogen and sulfur; in this embodiment, $R_3$, and $R_4$, may, for example, be independently selected from hydrogen, alkyl, and halo. In another embodiment, the ring carbon atom to which $R_3$ and $R_4$ are attached is a Spiro atom and $R_3$, $R_4$, and the spiro carbon atom to which they are attached, in combination, form a ring, typically containing three to seven ring atoms selected from carbon, oxygen, nitrogen and sulfur; in this embodiment, $R_1$ and $R_2$ may preferably be independently selected from hydrogen, alkyl, and halo In each of these embodiments, $R_5$ and $R_6$, in combination, may form a carbocyclic or heterocyclic ring fused to the A ring of the sultam of Formula 5 or Formula 6. For purposes of illustration, when $R_5$ and $R_6$, in combination, form a carbocyclic or heterocyclic ring, the sultam corresponds to Formula 7 or Formula 8:

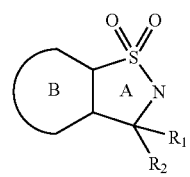

Formula 7

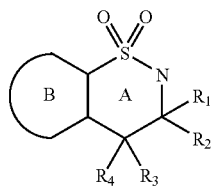

Formula 8 wherein the B ring is a carbocyclic or heterocyclic ring, and $R_1$, $R_2$, $R_3$, and $R_4$ are as defined in connection with Formulae 5 and 6. In one preferred embodiment, the B ring is an optionally substituted 5-membered heterocyclic ring or an optionally substituted 6-membered carbocyclic or heterocylic ring. Exemplary 5-membered and 6-membered heterocycles include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, homopiperidinyl, 1,2,3,6-tetrahydropyridinyl, 2-pyrrolinyl, 3-pyrrolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl. Examplary 5-membered and 6-membered aromatic heterocyclic groups include imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridyl, pyridazinyl, triazinyl, oxadiazolyl, thiadiazolyl, and furazanyl. By way of further example, the B ring may be an optionally substituted, fused cyclohexyl or phenyl ring with the substituent(s) being selected from lower alkyl, hydroxyl, alkoxyl, amino, halo, nitro and heterocylco. In another embodiment, the B ring may be an optionally substituted, fused pyridyl, pyrimidinyl, pyradizinyl, pyrizinyl, furyl, thienyl, isoxazolyl, or pyrrolyl; thus, for example, the B ring may be an optionally substituted, fused pyridyl, furyl, thienyl, or pyrrolyl ring with the substituent(s) being selected from lower alkyl, hydroxyl, alkoxyl, amino, halo, and nitro.

In another preferred embodiment, sultam 2 is a benzosultam corresponding to Formula 9 or Formula 10:

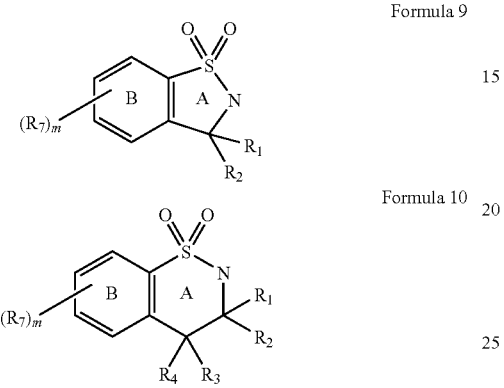

Formula 9

Formula 10 wherein $R_1$, $R_2$, $R_3$, and $R_4$ are independently hydrogen, hydrocarbyl, substituted hydrocarbyl, halo, hydroxyl, alkoxyl, amino, nitro, or heterocyclo, each $R_7$ is independently hydrocarbyl, substituted hydrocarbyl, halo, amino, nitro, alkoxyl, hydroxyl, acyl, acyloxy, or heterocyclo, and m is 0 to 4. Thus, for example, when sultam 2 corresponds to Formula 9 or Formula 10, m may be 1 to 4 and each $R_7$ may independently be alkyl, halo, amino, nitro, alkoxyl, hydroxyl, acyl or acyloxy. By way of further example, when sultam 2 corresponds to Formula 9 or Formula 10, m may be 1 to 4 and each $R_7$ may independently be alkyl, halo, alkoxyl, hydroxyl, or nitro. By way of further example, when sultam 2 corresponds to Formula 9 or Formula 10, m may be 1 to 4 and each $R_7$ may independently be alkyl, substituted alkyl, halo or nitro. By way of further example, when sultam 2 corresponds to Formula 9 or Formula 10, m may be 1 to 4 and each $R_7$ may be alkyl. In one embodiment in which sultam 2 is a benzosultam corresponding to Formula 9 or Formula 10, one of $R_1$ and $R_2$ is hydrogen and the other is hydrocarbyl, substituted hydrocarbyl, halo, hydroxyl, alkoxyl, or heterocycle; by way of example, in this embodiment, $R_1$ may be hydrogen and $R_2$ may be alkyl, aryl, or heterocycle (such as furyl). Similarly, in one such embodiment, one of $R_3$ and $R_4$ is hydrogen and the other is hydrocarbyl, substituted hydrocarbyl, halo, hydroxyl, alkoxyl, or heterocycle; by way of example, in this embodiment, $R_3$ may be hydrogen and $R_4$ may be alkyl, aryl, or heterocycle (such as furyl).

In one embodiment, commercially available metal porphyrin complexes such as Co(II)-tetraphenylporphine, Co(TPP), have been shown to be an effective catalyst for intramolecular nitrene insertion of C—H bonds with a broad range of arylsulfonyl azides, 21, leading to the high-yielding syntheses of corresponding benzosultam derivatives, 22, proceeding efficiently under mild and neutral conditions in low catalyst loading without the need of other reagents or additives, generating dinitrogen as the byproduct as illustrated in Reaction Scheme II.

Reaction Scheme II

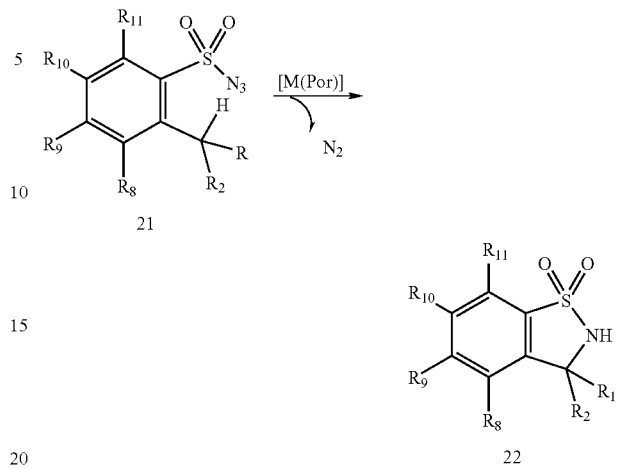

In this Reaction Scheme, $R_1$ and $R_2$ are as defined in connection with Formulae 5 and 6, and $R_8$, $R_9$, $R_{10}$, and $R_{11}$ are independently hydrogen, hydrocarbyl, substituted hydrocarbyl, halo, amino, nitro, alkoxyl, hydroxyl, acyl, acyloxy or heterocyclo. In one embodiment, $R_1$, $R_2$, $R_8$, $R_9$, $R_{10}$, and $R_{11}$ are independently hydrogen, alkyl, halo or nitro. In another embodiment, $R_1$, $R_2$, $R_8$, $R_9$, $R_{10}$, and $R_{11}$ are independently hydrogen, alkyl, or hydroxy. In another embodiment, $R_1$, $R_2$, $R_8$, $R_9$, $R_{10}$, and $R_{11}$ are independently hydrogen, alkyl, or amino. In another embodiment, the ring carbon atom to which $R_1$ and $R_2$ are attached is a spiro atom and $R_1$, $R_2$, and the Spiro carbon atom to which they are attached, in combination, form a ring, typically containing three to seven ring atoms selected from carbon, oxygen, nitrogen and sulfur; in this embodiment, $R_8$, $R_9$, $R_{10}$, and $R_{11}$ may have any of the values defined in connection with Formulae 22.

In another embodiment, commercially available metal porphyrin complexes, M(Por), such as Co(II)-tetraphenylporphine, Co(TPP), may be used as a catalyst for intramolecular nitrene insertion of C—H bonds with a broad range of arylsulfonyl azides, 23, in high-yielding syntheses of corresponding benzosultam derivatives, 24 as illustrated in Reaction Scheme III.

Reaction Scheme III

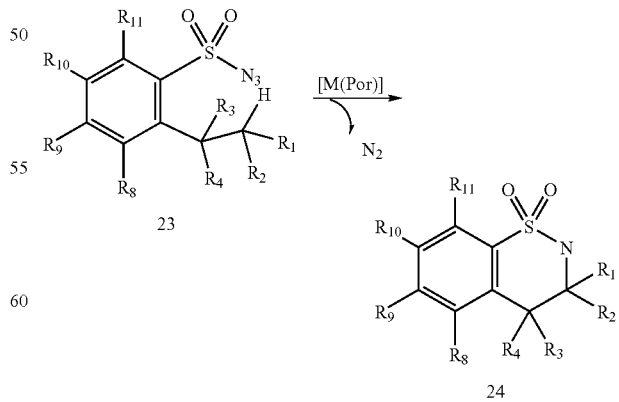

In this Reaction Scheme, $R_1$ and $R_2$ are as defined in connection with Formulae 5 and 6, and $R_8$, $R_9$, $R_{10}$, and $R_{11}$ are independently hydrogen, hydrocarbyl, substituted hydrocarbyl, halo, amino, nitro, alkoxyl, hydroxyl, acyl, acyloxy, or heterocyclo. In one embodiment, $R_1$, $R_2$, $R_8$, $R_9$, $R_{10}$, and $R_{11}$ are independently hydrogen, alkyl, halo or nitro In another embodiment, $R_1$, $R_2$, $R_8$, $R_9$, $R_{10}$, and $R_{11}$, are independently hydrogen, alkyl, or halo. In another embodiment, $R_1$, $R_2$, $R_8$, $R_9$, $R_{10}$, and $R_{11}$ are independently hydrogen, alkyl, or amino. In another embodiment, the ring carbon atom to which $R_1$ and $R_2$ are attached is a spiro atom and $R_1$, $R_2$, and the spiro carbon atom to which they are attached, in combination, form a ring, typically containing three to seven ring atoms selected from carbon, oxygen, nitrogen and sulfur; in this embodiment, $R_3$, $R_4$, $R_8$, $R_9$, $R_{10}$, and $R_{11}$ may have any of the values defined in connection with Formulae 24. In another embodiment, the ring carbon atom to which $R_3$ and $R_4$ are attached is a Spiro atom and $R_3$, $R_4$, and the spiro carbon atom to which they are attached, in combination, form a ring, typically containing three to seven ring atoms selected from carbon, oxygen, nitrogen and sulfur; in this embodiment, $R_1$, $R_2$, $R_8$, $R_9$, $R_{10}$, and $R_{11}$ may have any of the values defined in connection with Formulae 24.

As illustrated more fully in the examples, the regioselectivity of the nitrene insertion of C—H bonds to form the sultam can be influenced, at least in part, by selection of the metal porphyrin complex. As illustrated by entries 2k, 3k, 2l and 3l of Example 1 (see Table 3), the metal porphyrin selected for the catalysis may significantly influence regioselectivity. Continuous efforts are underway to identify suitable catalysts with greater regioselectivity toward either 5- or 6-membered ring formation.

Similarly, stereoselectivity of the reaction may also be influenced by the selection of chiral porphyrin ligands with desired electronic, steric, and chiral environments. See, e.g., Example 2. Accordingly, the catalytic system of the present invention may advantageously be used to control stereoselectivity.

In one embodiment, the metal of the metal porphyrin complex is a transition metal. Thus, for example, the metal may be any of the 30 metals in the 3d, 4d and 5d transition metal series of the Periodic Table of the Elements, including the 3d series that includes Sc, Ti, V, Cr, Mn, Fe, Co, Ni, Cu, and Zn; the 4d series that includes Y, Zr, Nb, Mo, Tc, Ru, Rh, Pd, Ag and Cd; and the 5d series that includes Lu, Hf, Ta, W, Re, Os, Ir, Pt, Au and Hg. In some embodiments, M is a transition metal from the 3d series. In some embodiments, M is selected from the group consisting of Co, Zn, Fe, and Ni. In some embodiments, M is Co.

The porphyrin with which the transition metal is complexed may be any of a wide range of porphyrins known in the art. Exemplary porphyrins are described in U.S. Patent Publication Nos. 2005/0124596 and 2006/0030718 and U.S. Pat. No. 6,951,935 (each of which is incorporated herein by reference, in its entirety).

In one embodiment, the metal porphyrin complex is a cobalt (II) porphyrin complex. In one particularly preferred embodiment, the cobalt porphyrin complex is an asymmetric porphyrin complex corresponding to the following structure

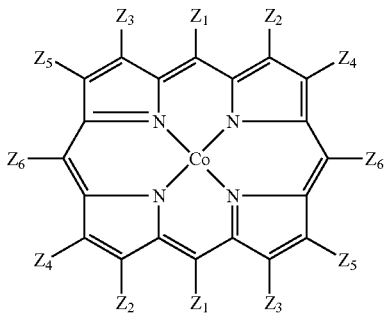

wherein each $Z_1$, $Z_2$, $Z_3$, $Z_4$, $Z_5$ and $Z_6$ are each independently selected from the group consisting of X, H, alkyl, substituted alkyls, arylalkyls, aryls and substituted aryls; and X is selected from the group consisting of halogen, trifluoromethanesulfonate (OTf), haloaryl and haloalkyl. In a preferred embodiment, $Z_2$, $Z_3$, $Z_4$, and $Z_5$ are hydrogen, $Z_1$ is substituted phenyl, and 4 is substituted phenyl and $Z_1$ and $Z_6$ are different. In one particularly preferred embodiment, $Z_2$, $Z_3$, $Z_4$, and $Z_5$ are hydrogen, $Z_1$ is substituted phenyl, and $Z_6$ is substituted phenyl and $Z_1$ and $Z_6$ are different and the porphyrin is a chiral porphyrin.

Exemplary cobalt (II) porphyrins include the following:

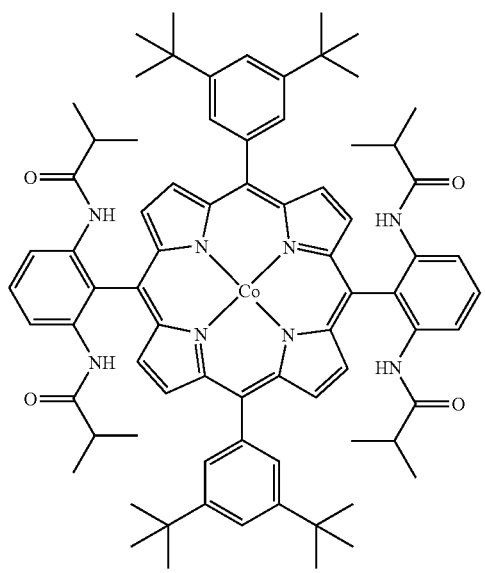

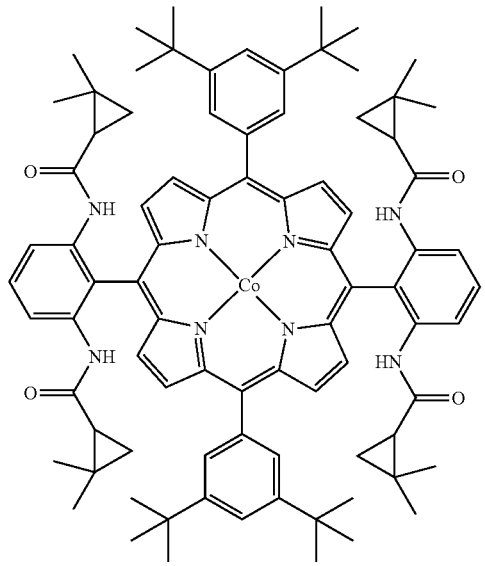

-continued

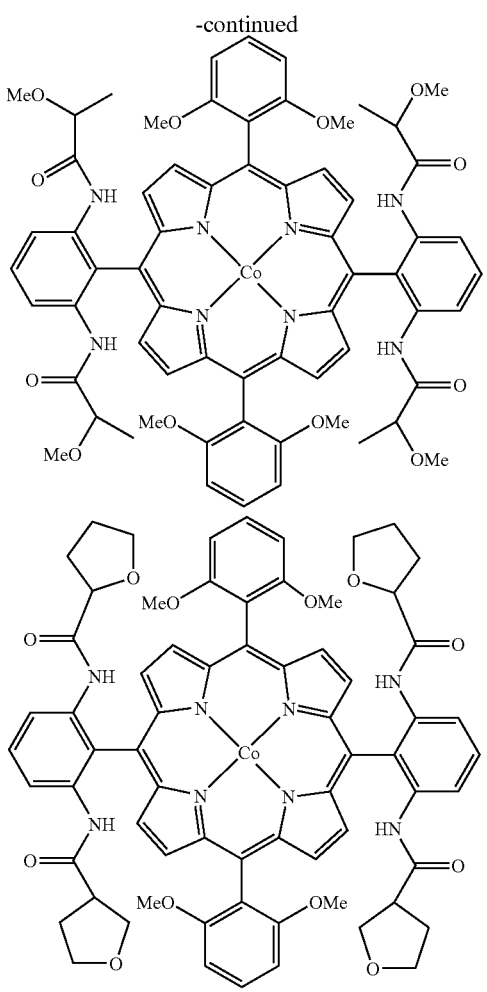

As noted, the C—H insertion reaction may be carried out under mild conditions, with relatively low catalyst loading (e.g., 0.5-2 mol % metal porphyrin complex), in a solvent such as chlorobenzene, methylene chloride or toluene, at temperatures of 20 to 80° C.

Definitions

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "heteroatom" shall mean atoms other than carbon and hydrogen.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like. The substituted alkyl groups described herein may have, as substituents, any of the substituents identified as substituted hydrocarbyl substituents.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term alkoxy or alkoxyl shall mean any univalent radical, RO— where R is an alkyl group.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The substituted aryl groups described herein may have, as substituents, any of the substituents identified as substituted hydrocarbyl substituents.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, R[1] is hydrocarbyl, heterosubstituted hydrocarbyl, or heterocyclo and R[2] is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl".

The term porphyrin refers to a compound comprising a fundamental skeleton of four pyrrole nuclei united through the a-positions by four methane groups to form the following macrocyclic structure:

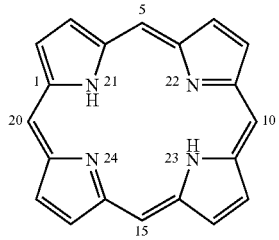

The following examples illustrate the invention.

EXAMPLE 1

Using the commercially available 2,4,6-triisopropylbenzenesulfonyl azide (1a) as a model substrate, we first surveyed potential catalytic activity of various metalloporphyrins (FIG. 1) toward intramolecular C—H amination (Table 1). The reactions were carried out with 2 mol % of metalloporphyrin at 80° C. overnight in chlorobenzene, which was identified previously as the solvent of choice for aziridination with DPPA. It was evident that Co(II) was by far the most active metal ion for the intramolecular C—H amination with TPP as the supporting ligand, forming the desired benzosultam 2a in 96% yield (Table 1, entry 5). While the V(IV), Cr(III), Mn(III), Ni(II), Cu(II) and Zn(II) complexes produced no or only trace amounts of 2a (Table 1, entries 1-3 and 6-8), Fe(TPP)Cl and Ru(TPP)(CO) could also catalyze the reaction to produce 2a in 11% and 67% yield, respectively (Table 1, entries 4 and 9). Control experiments showed that no reaction was observed in the absence of a catalyst (Table 1, entry 21). After the superiority of Co ion was established, several common porphyrins with different electronic and steric properties were applied to probe the ligand effect (FIG. 1). While both Co(OEP) and Co(TMeOPP) could effectively catalyze the reaction (Table 1, entries 10 and 11), an increase in ligand steric hindrance and/or electron deficiency resulted in poor catalytic activity (Table 1, entries 12-14). The Co(TPP)-catalyzed reaction could also proceed well at lower and even room temperatures (Table 1, entries 15 and 16) and in different solvents (Table 1, entries 17 and 18). A decrease in catalyst loading to 0.5 mol % had no dramatic effect on the catalytic process (Table 1, entries 19 and 20).

TABLE 1

Intramolecular Nitrene C—H Bond Insertion of 2,4,6-Triisopropylbenzenesulfonyl Azide Catalyzed by Metalloporphyrins.[a]

| entry | [M(Por)][b] | mol (%)[c] | solvent | temp (° C.) | yield (%)[d] |
|---|---|---|---|---|---|
| 1 | V(TPP)O | 2.0 | $C_6H_5Cl$ | 80 | 0 |
| 2 | Cr(TPP)Cl | 2.0 | $C_6H_5Cl$ | 80 | 0 |
| 3 | Mn(TPP)Cl | 2.0 | $C_6H_5Cl$ | 80 | <5[e] |
| 4 | Fe(TPP)Cl | 2.0 | $C_6H_5Cl$ | 80 | 11 |
| 5 | Co(TPP) | 2.0 | $C_6H_5Cl$ | 80 | 96 |
| 6 | Ni(TPP) | 2.0 | $C_6H_5Cl$ | 80 | 0 |
| 7 | Cu(TPP) | 2.0 | $C_6H_5Cl$ | 80 | 0 |
| 8 | Zn(TPP) | 2.0 | $C_6H_5Cl$ | 80 | 0 |
| 9 | Ru(TPP)(CO) | 2.0 | $C_6H_5Cl$ | 80 | 67 |
| 10 | Co(OEP) | 2.0 | $C_6H_5Cl$ | 80 | 86 |
| 11 | Co(TMeOPP) | 2.0 | $C_6H_5Cl$ | 80 | 93 |
| 12 | Co(TMP) | 2.0 | $C_6H_5Cl$ | 80 | 30 |
| 13 | Co(TPFPP) | 2.0 | $C_6H_5Cl$ | 80 | 8 |
| 14 | Co(TDClPP) | 2.0 | $C_6H_5Cl$ | 80 | 5 |
| 15 | Co(TPP) | 2.0 | $C_6H_5Cl$ | 40 | 95 |
| 16 | Co(TPP) | 2.0 | $C_6H_5Cl$ | 23 | 91 |
| 17 | Co(TPP) | 2.0 | $CH_2Cl_2$ | 23 | 91 |
| 18 | Co(TPP) | 2.0 | $C_6H_5CH_3$ | 23 | 85 |
| 19 | Co(TPP) | 0.5 | $C_6H_5Cl$ | 80 | 88 |
| 20 | Co(TPP) | 0.5 | $C_6H_5Cl$ | 80 | 92[f] |
| 21 | — | 0.0 | $C_6H_5Cl$ | 80 | 0 |

[a]Performed for 18 h under $N_2$ in the presence of 5Å molecular sieves with [1a] = 0.20 M.
[b]See FIG. 1 for structures.
[c]Catalyst loading
[d]Isolated yields.
[e]Estimated yield.
[f]Carried out for 42 h The Co(TPP)-based catalytic system was found to be suitable for a broad range of arylsulfonyl azides (Table 2), which were readily prepared from the corresponding aryl compounds. For each arylsulfonyl azide substrate, the catalytic reactions were evaluated at three different temperatures: 80° C., 40° C., and room temperature. In addition to intramolecular nitrene insertion into tertiary C—H bonds in 1a and 1b (Table 2, entries 1-2), secondary (Table 2, entries 3-4) and even primary (Table 2, entries 5-7) C—H bonds having various aromatic substitution patterns can be effectively aminated as well, resulting in selective formation of the corresponding 5-membered heterocycles. Although they all could be intramolecularly inserted in excellent yields at 80° C., the reactivity seemed to follow in the order of 3°>2°>1° C—H bonds. The difference in their reactivities became more noticeable when the reactions were conducted at lower temperatures (Table 2, entries 1-5). It is interesting to note that an increase in substitution on the aromatic ring led to higheryielding formation of the amination products (Table 2, entries 5-7), suggesting a positive buttressing effect of meta- and para-groups on the nitrene insertion of ortho-C—H bonds. Arylsulfonyl azides containing functional groups such as bromo and nitro at different positions could also be successfully catalyzed (Table 2, entries 8-9).

The aforementioned reactivity order of 3°>2°>1° C—H bonds, perhaps in combination with the higher reactivity of benzylic C—H bonds, resulted in exclusive formation of 5-membered ring structures in all the above cases where 1° and 3° or 1° and 2° C—H bonds coexist in the substrates (Table 2, entries 1-4 and 8-9). Azide 1j represents a case that contains both 2° and 3° C—H bonds (Table 2, entry 10). As in the other cases (Table 2, entries 1-4 and 8-9), the exclusive high-yielding formation of 5-membered spiroheterocyclic product was observed as a result of the reactivity order of 3°>2°>1° C—H bonds.

When an azide substrate containing different 2° C—H bonds such as benzylic and non-benzylic types was employed, however, both 5- and 6-membered ring formations were observed. For example, Co(TPP)-catalyzed intramolecular C—H amination of azide 1k with an n-butyl group led to the production of 6-membered 3k as well as the 5-membered 2k (Table 3, entries 1-3). The ratio of 2k to 3k was determined to be 72:28, 68:32, and 67:33 at 80° C., 40° C., and room temperature, respectively. The increase in the ratio of 2k to 3k at elevated temperature suggests the higher thermodynamic stability of the 5-membered ring structure. When 1l with an n-propyl group was used, both the 5-membered 2l and 6-membered 3l were similarly formed (Table 3, entries 4-6). The ratio of 5- to 6-membered ring product, which was 56:44, 56:44, and 54:46 at 80° C., 40° C., and room temperature, respectively, however, was significantly lower than the those of azide 1k reactions. Our preliminary results indicated that the ratio of 5- to 6-membered ring formation could be influenced with the use of different porphyrin ligands. While similar ratio of 2l to 3l was obtained for Co(TMP)- or Co(TMeOPP)-catalyzed reactions (Table 3, entries 7 and 8), the ratio was significantly increased to 73:27 when Co(OEP) was used as the catalyst (Table 3, entry 9).

TABLE 2

[Co(TPP)]-Catalyzed Intramolecular C—H Amination

| entry | azide | sultam | temp (° C.) | yield (%)[b] |
|---|---|---|---|---|
| 1 | 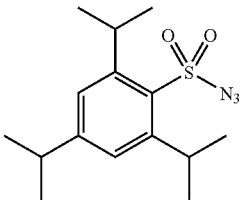 1a | 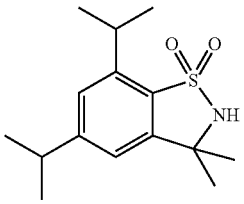 2a | 80<br>40<br>23 | 96<br>95<br>91 |
| 2 | 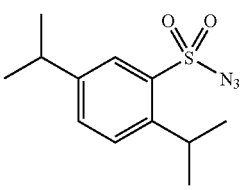 1b | 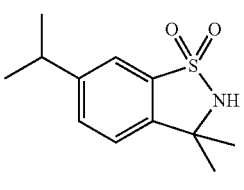 2b | 80<br>40<br>23 | 94<br>82<br>72 |
| 3 | 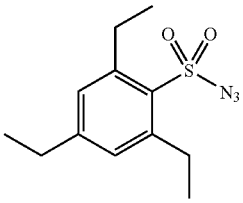 1c | 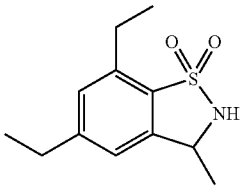 2c | 80<br>40<br>23 | 90<br>54<br>19 |
| 4 | 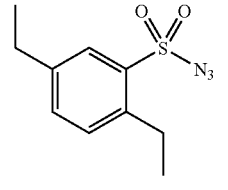 1d | 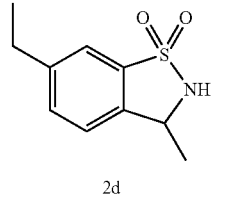 2d | 80<br>40<br>23 | 91<br>57<br>40 |

TABLE 2-continued

[Co(TPP)]-Catalyzed Intramolecular C—H Amination

| entry | azide | sultam | temp (° C.) | yield (%)[b] |
|---|---|---|---|---|
| 5 | 1e | 2e | 80<br>40<br>23 | 96<br>32<br>18 |
| 6 | 1f | 2f | 80<br>40<br>23 | 91<br>58<br>37 |
| 7 | 1g | 2g | 80<br>40<br>23 | 95<br>79<br>47 |
| 8 | 1h | 2h | 80<br>40<br>23 | 93<br>77<br>46 |
| 9 | 1i | 2i | 80<br>40<br>23 | 99<br>85<br>69 |
| 10 | 1j | 2j | 80<br>40<br>23 | 87<br>33<br>23 |

[a]Reactions were performed in chlorobenzene at 80° C. for 18 h under $N_2$ with 2 mol % [Co(TPP)] in the presence of 5Å molecular sieves with a azide concentration of 0.20 M.
[b]Isolated yields.

TABLE 3

Five- and Six-Membered Ring Formations via Intramolecular C—H Amination Catalyzed by Cobalt Porphyrins.[a]

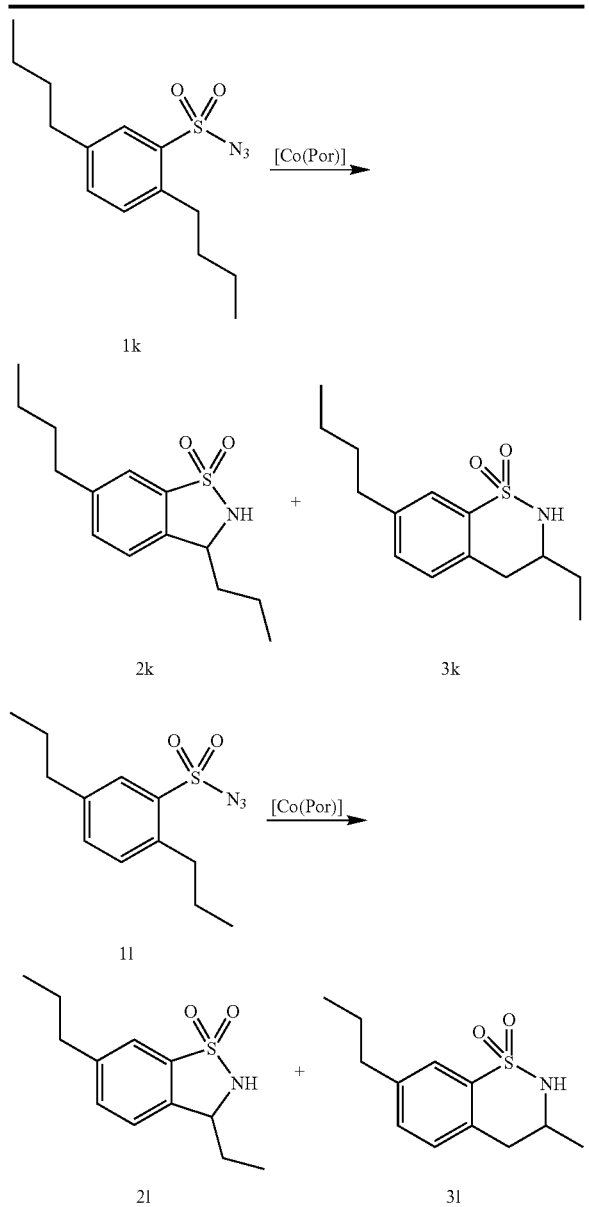

| entry | azide | [Co(Por)][b] | temp (° C.) | sultam | distribution[c] | yield (%)[d] |
|---|---|---|---|---|---|---|
| 1 | 1k | Co(TPP) | 80 | 2k + 3K | 72 + 28 | 91 |
| 2 | 1k | Co(TPP) | 40 | 2k + 3K | 68 + 32 | 41 |
| 3 | 1k | Co(TPP) | 23 | 2k + 3K | 67 + 33 | 25 |
| 4 | 1l | Co(TPP) | 80 | 2l + 3l | 56 + 44 | 94 |
| 5 | 1l | Co(TPP) | 40 | 2l + 3l | 56 + 44 | 56 |
| 6 | 1l | Co(TPP) | 23 | 2l + 3l | 54 + 46 | 33 |
| 7 | 1l | Co(TMP) | 80 | 2l + 3l | 55 + 45 | 77 |
| 8 | 1l | Co(TMeOPP) | 80 | 2l + 3l | 59 + 41 | 97 |
| 9 | 1l | Co(OEP) | 80 | 2l + 3l | 73 + 27 | 92 |

[a]Performed in $C_6H_5Cl$ for 18 h under $N_2$ with 2 mol % [Co(Por)] in the presence of 5 Å MS; [azide] = 0.20 M.
[b]See FIG. 1 for structures.
[c]Ratio of 5- to 6-membered ring products determined by NMR.
[d]Combined isolated yields of 5- and 6-membered ring products

Supporting Information

All intramolecular C—H amination reactions were performed under nitrogen in oven-dried glassware following standard Schlenk techniques. 5 Å molecular sieves were dried in a vacuum oven prior to use. Chlorobenzene and dichloromethane were dried over calcium hydride under nitrogen and freshly distilled before use, and toluene was distilled under nitrogen from sodium benzophenone ketyl. 2,4,6-Triisopropylbenzenesulfonyl azide was purchased from Alfa Aesar and used without further purification. Substituted benzenes and sulfonyl chlorides were purchased from commercial sources and used without further purification. Thin layer chromatography was performed on Merck TLC plates (silica gel 60 F254). Flash column chromatography was performed with ICN silica gel (60 Å, 230-400 mesh, 32-63 μm). [13]H NMR and $^{13}$C NMR were recorded on a Varian Inova400 (400 MHz) or a Varian Inova500 (500 MHz) instrument with chemical shifts reported relative to residual solvent. Infrared spectra were measured with a Nicolet Avatar 320 spectrometer with a Smart Miracle accessory. HRMS data was obtained on an Agilent 1100 LC/MS ESI/TOF mass spectrometer.

Note on Safety: Careful control experiments showed the arylsulfonyl azides reported in this work were stable under the conditions used. But it should be noted that some of the azide compounds may be explosive and should be handled with great care.

General Procedure for the Synthesis of Sulfonyl Chlorides: A round bottom flask was purged with $N_2$ and charged with the substituted benzene and chloroform (2.0 ml/mmol sub. benzene). The resulting solution was cooled in an ice bath to 0° C. Chlorosulfonic acid (4.5 eq) was added to the flask via a syringe over 10 minutes and was stirred under $N_2$ atmosphere until the reaction was complete (monitored by TLC/ developed in $I_2$-approximately 3-4 hrs). Upon reaction completion, the mixture was carefully poured over crushed ice and the aqueous layer was extracted with chloroform (3×5 ml). The combined organic layers were then washed with brine (10 ml), dried over sodium sulfate, and concentrated by rotary evaporation to give the crude product. The resulting oil was then purified by flash column chromatography (9:1, hexanes:ethyl acetate).

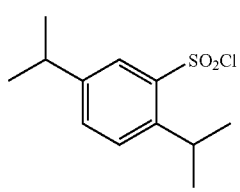

2,5-Diisopropylbenzene-1-sulfonyl chloride was obtained from 1,4-diisopropylbenzene using the general procedure as a white solid in 96% yield (1.25 g). $^1$H NMR (400 MHz, $CDCl_3$): δ7.87 (d, J=1.6 Hz, 1H), 7.52 (m, 2H), 4.02 (sept, J=6.8 Hz, 1H), 2.97 (sept, J=6.8 Hz, 1H), 1.33 (d, J=7.2 Hz, 6H), 1.29 (d, J=6.8 Hz, 6H). $^{13}$C NMR (100 MHz, $CDCl_3$): δ147.4, 146.4, 142.0, 133.6, 128.8, 126.1, 33.7, 28.7, 23.7, 23.6. IR (neat, $cm^{-1}$): 2963, 1490, 1362, 1167.

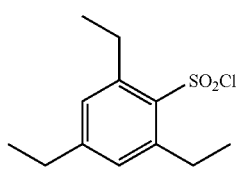

2,4,6-Triethylbenzene-1-sulfonyl chloride was obtained from 1,3,5-triethylbenzene using the general procedure as a yellow oil in 99% yield (778 mg). $^1$H NMR (400 MHz, CDCl$_3$): δ7.0 (s, 2H), 3.15 (q, J=7.2 Hz, 4H), 2.66 (q, J=7.2 Hz, 2H), 1.32 (m, 6H), 1.26 (m, 3H); $^{13}$C NMR (100 MHz, CDCl$_3$): δ151.5, 145.7, 139.5, 129.7, 28.5, 28.3, 16.1, 14.7. IR (neat, cm$^{-1}$): 2969, 1595, 1366, 1184, 1172.

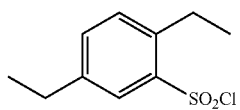

2,5-Diethylbenzene-1-sulfonyl chloride was obtained from 1,4-diethylbenzene using the general procedure as colorless oil in 94% yield (1.64 g). $^1$H NMR (400 MHz, CDCl$_3$): δ7.88 (d, J=1.2 Hz, 1H), 7.48 (dd, J=8.0, 1.6 Hz, 1H), 7.38 (d, J=8.0, 1H), 3.16 (q, J=7.2 Hz, 2H), 2.71 (q, J=7.6 Hz, 2H), 1.34 (t, J=7.2 Hz, 3H), 1.27 (t, J=7.6 Hz, 3H). $^{13}$C NMR (100 MHz, CDCl$_3$): δ143.0, 142.5, 141.1, 134.9, 131.5, 127.9, 28.1, 25.35, 15.23, 15.02. IR (neat, cm$^{-1}$): 2968, 1366, 1172.

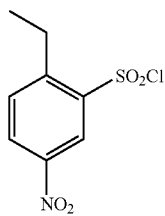

2-Ethyl-5-nitrobenzene-1-sulfonyl chloride was obtained from 1-ethyl-4-nitrobenzene using the literature procedure as tan oil in 83% yield (1.37 g). $^1$H NMR (400 MHz, CDCl$_3$): δ8.93 (d, J=2.0 Hz, 1H), 8.50 (dd, J=2.0, 8.0 Hz, 1H), 7.71 (d, J=8.4 Hz, 1H), 3.31 (q, J=7.2 Hz, 2H), 1.42 (t, J=7.2 Hz, 3H); $^{13}$C NMR (100 MHz, CDCl$_3$): δ151.1, 145.8, 143.4, 132.9, 129.2, 124.3, 26.0, 14.7. IR (neat, cm$^{-1}$): 3108, 1526, 1347.

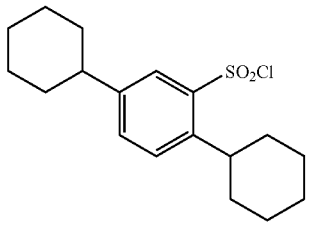

2,5-Dicyclohexylbenzene-1-sulfonyl chloride was obtained from 1,4-dicyclohexylbenzene using the general procedure as a white solid in 98% yield (1.37 g). $^1$H NMR (400 MHz, CDCl$_3$): δ7.85 (s, 1H), 7.48 (m, 2H), 3.65-3.58 (m, 1H), 2.56-2.53 (m, 1H), 1.94-1.74 (m, 10H), 1.56-1.26 (m, 10H). $^{13}$C NMR (100 MHz, CDCl$_3$): δ146.5, 145.1, 142.1, 133.8, 129.5, 126.5, 43.9, 39.3, 34.0, 33.9, 26.6, 26.0, 25.8. IR (neat, cm$^{-1}$): 2924, 2850, 1448, 1361, 1163. HRMS (ESI): Calcd. for C$_{18}$H$_{29}$NClO$_2$S ([M+NH$_4$]$^+$) m/z 358.1602, Found 358.1625.

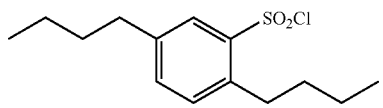

2,5-Dibutylbenzene-1-sulfonyl chloride was obtained from 1,4-dibutylbenzene using the general procedure as colorless oil in 81% yield (2.45 g). $^1$H NMR (400 MHz, CDCl$_3$): δ7.86 (d, J=1.6 Hz, 1H), 7.43 (dd, J=1.6, 8.0 Hz, 1H), 7.34 (d, J=8.0 Hz, 1H), 3.08 (t, J=8.0 Hz, 2H), 2.66 (t, J=7.6 Hz, 2H), 1.69 (m, 2H), 1.61 (m, 2H), 1.47 (sextet, J=7.6 Hz, 2H), 1.36 (sextet, J=7.6 Hz, 2H), 0.97 (t, J=7.6 Hz, 3H), 0.94 (t, J=7.6 Hz, 3H). $^{13}$C NMR (100 MHz, CDCl$_3$): δ142.5, 141.8, 140.0, 135.2, 132.1, 128.4, 34.9, 33.1, 32.0, 22.7, 22.2, 13.8. IR (neat, cm$^{-1}$): 2957, 2931, 1370, 1174. HRMS (ESI): Calcd. for C$_{14}$H$_{25}$NClO$_2$S ([M+NH$_4$]$^+$) m/z 306.1295, Found 306.1287.

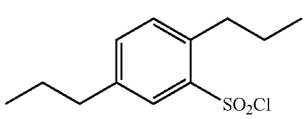

2,5-Dipropylbenzene-1-sulfonyl chloride was obtained from 1,4-dipropylbenzene using the general procedure as colorless oil in 91% yield (2.93 g). $^1$H NMR (400 MHz, CDCl$_3$): δ7.86 (d, J=1.6 Hz, 1H), 7.43 (dd, J=1.6, 8.0 Hz, 1H), 7.35 (d, J=8.0 Hz, 1H), 3.06 (t, J=8 Hz, 2H), 2.64 (t, J=7.6 Hz, 2H), 1.74 (q, J=8.0 Hz, 2H), 1.66 (q, J=7.6 Hz, 2H), 1.04 (t, J=7.6 Hz, 3H), 0.95 (t, J=7.6 Hz, 3H). $^{13}$C NMR (100 MHz, CDCl$_3$): δ142.8, 141.8, 139.8, 135.4, 132.37, 128.7, 37.4, 34.4, 24.4, 24.3, 14.3, 13.8. IR (neat, cm$^{-1}$): 2962, 1369, 1174.

General Procedure for the Synthesis of Sulfonyl Azides: A solution of the sulfonyl chloride (1-10 mmol) in water: acetone (1:1, 6 ml/mmol) was stirred in a round bottom flask and cooled in an ice bath to 0° C. for 15-20 minutes. Sodium azide (1.5 eq) was added in portions to the sulfonyl chloride mixture and the reaction was monitored by TLC to completion (typically 2-5 hrs). After the reaction was complete, the flask underwent rotary evaporation until the acetone was removed. The crude product was extracted from the water using ethyl acetate or dichloromethane (3×5 ml/mmol). It was then washed with brine (10 ml/mmol), dried over sodium sulfate, and concentrated by rotary evaporation. The resulting oil was then purified by flash column chromatography (9:1, hexanes: ethyl acetate). The fractions containing product were collected and concentrated by rotary evaporation to afford the pure compound.

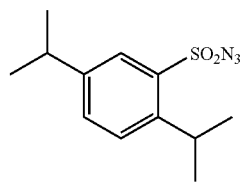

2,5-Diisopropylbenzene-1-sulfonyl azide (1b, Table 2, Entry 2) was obtained from 2,5-diisopropylbenzene-1-sulfonyl chloride using the general procedure as a white solid in 98% yield (603 mg). $^1$H NMR (400 MHz, CDCl$_3$): δ7.23 (s, 1H), 7.50 (m, 2H), 3.70 (sept, J=6.8 Hz, 1H), 2.97 (sept, J=6.8 Hz, 1H), 1.30-1.27 (m, 12H); $^{13}$C NMR (100 MHz, CDCl$_3$): δ147.2, 146.8, 135.6, 133.1, 128.5, 126.9, 33.6, 29.3, 24.0, 23.6. IR (neat, cm$^{-1}$): 2964, 2123, 1361, 1161. HRMS (ESI): Calcd. for C$_{12}$H$_{21}$NN$_3$O$_2$S ([M+NH$_4$]$^+$) m/z 285.1385, Found 285.1379.

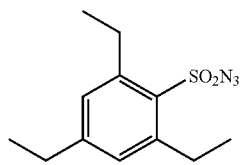

2,4,6-Triethylbenzene-1-sulfonyl azide (1c, Table 2, Entry 3) was obtained from 2,4,6-triethylbenzene-1-sulfonyl chloride using the general procedure as colorless oil in 95% yield (487 mg). $^1$H NMR (400 MHz, CDCl$_3$): δ7.0 (s, 2H), 3.02 (q, J=7.2 Hz, 4H), 2.62 (q, J=7.6 Hz, 2H), 1.27-1.20 (m, 9H). $^{13}$C NMR (100 MHz, CDCl$_3$): δ150.6, 146.3, 132.4, 129.6, 28.5, 28.3, 16.7, 14.7. IR (neat, cm$^{-1}$): 2968, 2119, 1597, 1363, 1162. HRMS (ESI): Calcd. for C$_{12}$H$_{21}$N$_4$O$_2$S ([M+NH$_4$]$^+$) m/z 285.1385, Found 285.1373.

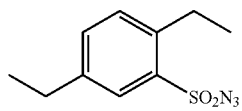

2,5-Diethylbenzene-1-sulfonyl azide (1d, Table 2, Entry 4) was obtained from 2,5-diethylbenzene-1-sulfonyl chloride using the general procedure as colorless oil in 94% yield (481 mg). $^1$H NMR (400 MHz, CDCl$_3$): δ7.83 (d, J=1.6 Hz, 1H), 7.44 (dd, J=1.2, 7.6 Hz, 1H), 7.35 (d, J=8.0 Hz, 1H), 2.98 (q, J=7.6 Hz, 2H), 2.69 (q, J=7.6 Hz, 2H), 1.28 (t, J=7.6 Hz, 3H), 1.25 (t, J=7.6 Hz, 3H). $^{13}$C NMR (100 MHz, CDCl$_3$): δ142.8, 141.6, 136.1, 134.3, 131.3, 128.5, 28.19, 25.6, 15.3, 15.2. IR (neat, cm$^{-1}$): 2970, 2123, 1363, 1164, 1190. HRMS (ESI): Calcd. for C$_9$H$_{17}$N$_4$O$_2$S ([M+NH$_4$]$^+$) m/z 243.0916, Found 243.0915.

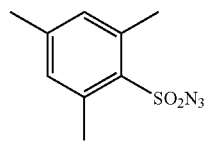

2,4,6-Trimethylbenzene-1-sulfonyl azide (1e, Table 2, Entry 5) was obtained from 2,4,6-trimethylbenezne-1-sulfonyl chloride using the general procedure as a tan oil in 93% yield (480 mg). $^1$H NMR (400 MHz, CDCl$_3$): δ7.01 (s, 2H), 2.66 (s, 6H), 2.33 (s, 3H). $^{13}$C NMR (125 MHz, CDCl$_3$): δ144.5, 139.8, 133.1, 132.0, 22.67, 21.03. IR (neat, cm$^{-1}$): 2980, 2120, 1601, 1363, 1188, 1163.

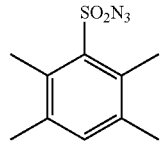

2,3,5,6-Tetramethylbenzene-1-sulfonyl azide (1f, Table 2, Entry 6) was obtained from 2,3,5,6-tetramethylbenzene-1-sulfonyl chloride using the general procedure as a white solid in 84% yield (1.73 g). $^1$H NMR (400 MHz, CDCl$_3$): δ7.23 (s, 1H), 2.56 (s, 6H), 2.30 (s, 6H). $^{13}$C NMR (125 MHz, CDCl$_3$): δ137.3, 137.7, 136.4, 135.7, 20.84, 17.87. IR (neat, cm$^{-1}$): 2920, 2119, 1349, 1157. HRMS (ESI): Calcd. for C$_{10}$H$_{17}$N$_4$O$_2$S ([M+NH$_4$]$^+$) m/z 257.1072, Found 257.1070.

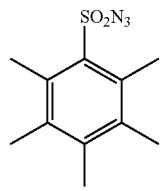

2,3,4,5,6-Pentamethylbenzene-1-sulfonyl azide (1g, Table 2, Entry 7) was obtained from 2,3,4,5,6-pentamethylbenzene-1-sulfonyl chloride using the general procedure as a white solid in 98% yield (2.02 g). $^1$H NMR (400 MHz, CDCl$_3$): δ2.59 (s, 6H), 2.31 (s, 3H), 2.27 (s, 6H). $^{13}$C NMR (125 MHz, CDCl$_3$): δ141.8, 135.5, 135.3, 134.9, 19.01, 17.97, 17.00. IR (neat, cm$^{-1}$): 2927, 2121, 1348, 1152. HRMS (ESI): Calcd. for C$_{11}$H$_{19}$N$_4$O$_2$S ([M+NH$_4$]$^+$) m/z 271.1229, Found 271.1227.

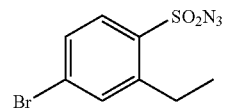

4-Bromo-2-ethylbenzene-1-sulfonyl azide (1h, Table 2, Entry 8) was obtained from 4-bromo-2-ethylbenzene-1-sulfonyl chloride using the general procedure as a white solid in 98% yield (486 mg). $^1$H NMR (400 MHz, CDCl$_3$): δ7.89 (d, J=8.0 Hz, 1H), 7.61 (d, J=2.0 Hz, 1H), 7.53 (dd, J=2.0, 8.0 Hz, 1H), 3.01 (q, J=7.2 Hz, 2H), 1.32 (t, J=7.6 Hz, 3H); $^{13}$C NMR (100 MHz, CDCl$_3$): δ146.4, 135.4, 134.3, 130.8, 130.1, 129.6, 25.97, 14.88. IR (neat, cm$^{-1}$): 2979, 2126, 1579, 1364, 1164.

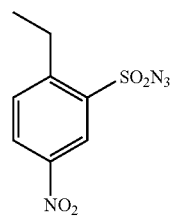

2-Ethyl-5-nitrobenzene-1-sulfonyl azide (1i, Table 2, Entry 9) was obtained from 2-ethyl-5-nitrobenzene-1-sulfonyl chloride using the general procedure as a yellow solid in 92% yield (472 mg). $^1$H NMR (400 MHz, CDCl$_3$): δ8.89 (d, J=2.4 Hz, 1H), 8.46 (dd, J=2.4, 8.8 Hz, 1H), 7.68 (d, J=8.4 Hz, 1H), 3.15 (q, J=7.6 Hz, 2H), 1.38 (t, J=7.6 Hz, 3H). $^{13}$C NMR (100 MHz, CDCl$_3$): δ151.6, 145.8, 138.1, 132.6, 128.8, 124.6, 26.43, 14.84. IR (neat, cm$^{-1}$): 2972, 2141, 1522, 1349, 1168.

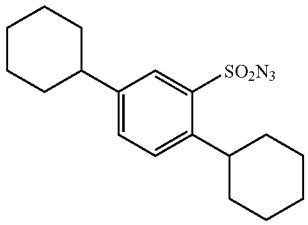

2,5-Dicyclohexylbenzene-1-sulfonyl azide (1j, Table 2, Entry 10) was obtained from 2,5-dicyclohexylbenzene-1-sulfonyl chloride using the general procedure as a white solid in 99% yield (502 mg). $^1$H NMR (400 MHz, CDCl$_3$): δ7.84 (s, 1H), 7.45 (m, 2H), 3.28 (m, 1H), 2.56 (m, 1H), 1.83 (m, 10H), 1.34 (m, 10H). $^{13}$C NMR (125 MHz, CDCl$_3$): δ146.3, 145.5, 135.8, 133.2, 129.2, 127.4, 43.85, 40.01, 34.31, 34.10, 26.66, 26.62, 26.00, 25.87. IR (neat, cm$^{-1}$): 2924, 2852, 2122, 1364, 1164. HRMS (ESI): Calcd. for C$_{18}$H$_{29}$N$_4$O$_2$S ([M+NH$_4$]$^+$) m/z 365.2011, Found 365.2005.

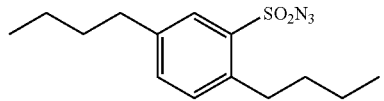

2,5-Dibutylbenzene-1-sulfonyl azide (1k, Table 3, Entries 1-3) was obtained from 2,5-dibutylbenzene-1-sulfonyl chloride using the general procedure as colorless oil in 98% yield (1.00 g). $^1$H NMR (400 MHz, CDCl$_3$): δ7.83 (s, 1H), 7.42 (d, J=8.0 Hz, 1H), 7.32 (d, J=8.0 Hz, 1H), 2.92 (t, J=8.0 Hz, 2H), 2.64 (t, J=8.0 Hz, 2H), 1.67-1.52 (m, 4H), 1.47-1.39 (m, 2H), 1.38-1.29 (m, 2H), 0.95-0.90 (m, 6H). $^{13}$C NMR (125 MHz, CDCl$_3$): δ141.5, 140.4, 136.1, 134.6, 131.9, 129.1, 34.89, 33.48, 33.23, 32.40, 22.79, 22.22, 13.86, 13.82. IR (neat, cm$^{-1}$): 2958, 2931, 2872, 2123, 1367, 1165. HRMS (ESI): Calcd. for C$_{14}$H$_{25}$N$_4$O$_2$S ([M+NH$_4$]$^+$) m/z 313.1698, Found 313.1689.

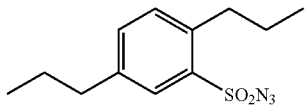

2,5-Dipropylbenzene-1-sulfonyl azide (1l, Table 3, Entries 4-9) was obtained from 2,5-dipropylbenzene-1-sulfonyl chloride using the general procedure as colorless oil in 78% yield (803 mg). $^1$H NMR (400 MHz, CDCl$_3$): δ7.83 (s, 1H), 7.41 (d, J=7.6 Hz, 1H), 7.34 (d, J=8.0 Hz, 1H), 2.92 (t, J=7.6 Hz, 2H), 2.64 (t, J=7.2 Hz, 2H), 1.73-1.63 (m, 4H), 1.02 (t, J=7.6 Hz, 3H), 0.95 (t, J=7.2 Hz, 3H). $^{13}$C NMR (125 MHz, CDCl$_3$): δ141.3, 140.2, 136.1, 134.7, 131.9, 129.1, 37.18, 34.60, 24.49, 24.21, 14.10, 13.61. IR (neat, cm$^{-1}$): 2962, 2933, 2123, 1365, 1165. HRMS (ESI): Calcd. for C$_{12}$H$_{21}$N$_4$O$_2$S ([M+NH$_4$]$^+$) m/z 285.1385, Found 285.1379.

General Procedure for Intramolecular C—H Amination. An oven dried Schlenk tube, that was previously evacuated and backfilled with nitrogen gas, was charged with azide (if solid, 0.2 mmol), catalyst (0.004 mmol), and 5 Å MS (100 mg). The Schlenk tube was then evacuated and back filled with nitrogen. The Teflon screw cap was replaced with a rubber septum and 0.5 ml of solvent was added followed by azide (if liquid, 0.2 mmol) and the remaining solvent (total 1mL). The Schlenk tube was then purged with nitrogen for 2 minutes and the rubber septum was replaced with a Teflon screw cap. The Schlenk tube was then placed in an oil bath for the desired time and temperature. Following completion of the reaction, the reaction mixture was concentrated and purified by dry loading the sample on a Teledyne flash chromatography instrument running a gradient solvent system of 100:0 (hexanes:ethyl acetate) to 50:50 (hexanes:ethyl acetate). The fractions containing product were collected and concentrated by rotary evaporation to afford the pure compound.

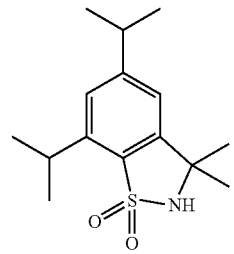

2a (Table 2, Entry 1) was synthesized by the general procedure from 2,4,6-triisopropylbenzene-1-sulfonyl azide (1a) as a tan solid in 96% yield (54.2 mg). $^1$H NMR (400 MHz, CDCl$_3$): δ7.21 (s, 1H), 6.98 (s, 1H), 4.68 (s, 1H), 3.60 (heptet, J=6.8 Hz, 1H), 2.97 (heptet, J=6.8 Hz, 1H), 1.62 (s, 6H), 1.34 (d, J=6.8 Hz, 6H), 1.26 (d, J=6.8 Hz, 6H). $^{13}$C NMR (100 MHz, CDCl$_3$): δ155.4, 146.7, 145.2, 130.8, 124.2, 117.7, 59.72, 34.58, 29.81, 29.38, 23.81, 23.51. IR (neat, cm$^{-1}$): 3244, 2960, 2922, 2865, 1598, 1459, 1382, 1295, 1172, 1151, 1129. HRMS (ESI): Calcd. for C$_{15}$H$_{23}$NO$_2$SNa ([M+Na]$^+$) m/z 304.13417, Found 304.13441.

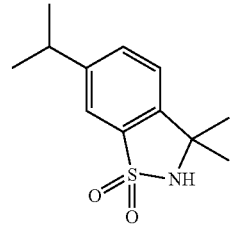

2b (Table 2, Entry 2) was synthesized by the general procedure from 2,5-diisopropylbenzene-1-sulfonyl azide (1b) as a tan solid in 94% yield (45.0 mg). $^1$H NMR (400 MHz, CDCl$_3$): δ7.57 (s, 1H), 7.47 (dd, J=8.0, 1.2 Hz, 1H), 7.28 (d, J=8.0 Hz, 1H), 4.61 (s, 1H), 3.00 (heptet, J=7.2 Hz, 1H), 1.63 (s, 6H), 1.27 (d, J=7.2 Hz, 6H). $^{13}$C NMR (100 MHz, CDCl$_3$): δ150.5, 143.5, 135.1, 132.1, 122.5, 118.4, 60.62, 33.95, 29.68, 23.71. IR (neat, cm$^{-1}$): 3240, 2965, 2930, 2899, 2871, 1486, 1463, 1382, 1302, 1277, 1158, 1143, 1122, 1073. HRMS (ESI): Calcd. for C$_{12}$H$_{18}$NO$_2$S ([M+H]$^+$) m/z 240.10528, Found 240.10532.

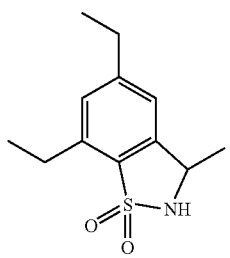

2c (Table 2, Entry 3) was synthesized by the general procedure from 2,4,6-triethylbenzene-1-sulfonyl azide (1c) as a tan oil in 90% yield (43.2 mg). $^1$H NMR (400 MHz, CDCl$_3$): δ7.11 (s, 1H), 6.96 (s, 1H), 4.68 (m, 1H), 4.64 (m, 1H), 2.98 (q, J=7.6 Hz, 2H), 2.70 (q, J=7.6 Hz, 2H), 1.57 (d, J=6.8 Hz, 3H), 1.33 (t, J=7.6 Hz, 3H), 1.25 (t, J=7.6 Hz, 3H). $^{13}$C NMR (100 MHz, CDCl$_3$): δ150.6, 142.4, 140.1, 131.3, 128.6, 120.2, 52.64, 28.99, 24.62, 21.55, 15.36, 14.57. IR (neat, cm$^{-1}$): 3251, 2976, 2935, 2875, 1600, 1459, 1374, 1279, 1174, 1146. HRMS (ESI): Calcd. for C$_{12}$H$_{18}$NO$_2$S ([M+H]$^+$) m/z 240.10528, Found 240.10416.

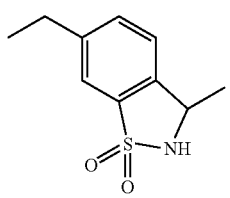

2d (Table 2, Entry 4) was synthesized by the general procedure from 2,5-diethylbenzene-1-sulfonyl azide (1d) as a tan oil in 91% yield (38.6 mg). $^1$H NMR (400 MHz, CDCl$_3$): δ7.57 (s, 1H), 7.44 (d, J=8.0 Hz, 1H), 7.27 (d, J=8.0 Hz, 1H), 4.81 (s, 1H), 4.78-4.70 (m, 1H), 2.74 (q, J=7.6 Hz, 2H), 1.58 (d, J=6.8 Hz, 3H), 1.26 (t, J=7.6 Hz, 3H). $^{13}$C NMR (100 MHz, CDCl$_3$): δ146.2, 139.3, 135.7, 133.5, 123.8, 120.1, 53.40, 28.77, 21.75, 15.46. IR (neat, cm$^{-1}$): 3256, 2932, 1489, 1455, 1417, 1372, 1282, 1211, 1150. HRMS (ESI): Calcd. for C$_{10}$H$_{14}$NO$_2$S ([M+H]$^+$) m/z 212.07398, Found 212.07422.

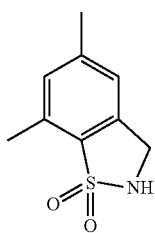

2e (Table 2, Entry 5) was synthesized by the general procedure from 2,4,6-trimethylbenzene-1-sulfonyl azide (1e) as a tan solid in 96% yield (38.1 mg). $^1$H NMR (400 MHz, CDCl$_3$): δ7.04 (s, 1H), 6.94 (s, 1H), 4.87 (s, 1H), 4.42 (d, J=5.2 Hz, 2H), 2.56 (s, 3H), 2.38 (s, 3H). $^{13}$C NMR (100 MHz, CDCl$_3$): δ144.0, 137.2, 133.9, 131.5, 131.3, 122.2, 45.06, 21.44, 16.78. IR (neat, cm$^{-1}$): 3236, 2957, 2920, 1594, 1447, 1379, 1281, 1170, 1146. HRMS (ESI): Calcd. for C$_9$H$_{12}$NO$_2$S ([M+H]$^+$) m/z 198.05833, Found 198.05891.

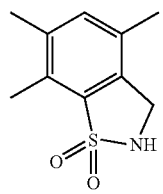

2f (Table 2, Entry 6) was synthesized by the general procedure from 2,3,5,6-tetramethylbenzene-1-sulfonyl azide (1f) as a tan solid in 91% yield (38.5 mg). $^1$H NMR (400 MHz, CDCl$_3$): δ7.15 (s, 1H), 4.79 (s, 1H), 4.32 (d, J=5.2 Hz, 2H), 2.49 (s, 3H), 2.29 (s, 3H), 2.19 (s, 3H). $^{13}$C NMR (125 MHz, DMSO): δ140.0, 136.1, 133.1, 132.1, 129.6, 127.5, 43.40, 16.16, 15.34, 14.37, 14.27. IR (neat, cm$^{-1}$): 3269, 2959, 2929, 2858, 1727, 1490, 1460, 1382, 1268, 1138, 1072, 1038. HRMS (ESI): Calcd. for C$_{10}$H$_{14}$NO$_2$S ([M+H]$^+$) m/z 212.07398, Found 212.07460.

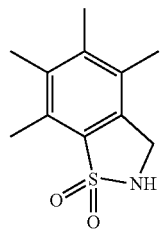

2g (Table 2, Entry 7) was synthesized by the general procedure from 2,3,4,5,6-pentamethylbenzene-1-sulfonyl azide (1g) as a tan solid in 95% yield (42.6 mg). $^1$H NMR (400 MHz, CDCl$_3$): δ4.89 (s, 1H), 4.33 (d, J=5.2 Hz, 2H), 2.53 (s, 3H), 2.25 (s, 3H), 2.36 (s, 3H), 2.12 (s, 3H). $^{13}$C NMR (125 MHz, DMSO): δ137.5, 134.8, 134.5, 133.6, 131.2, 127.9, 42.81, 18.38, 16.35, 13.13. IR (neat, cm$^{-1}$): 3250, 2957, 2929, 2871, 1728, 1458, 1378, 1272, 1200, 1148, 1072, 1036. HRMS (ESI): Calcd. for C$_{11}$H$_{16}$NO$_2$S ([M+H]$^+$) m/z 226.08963, Found 226.08941.

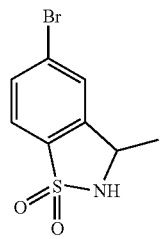

2h (Table 2, Entry 8) was synthesized by the general procedure from 4-bromo-2-ethylbenzene-1-sulfonyl azide (1h) as a tan solid in 93% yield (48.9 mg). $^1$H NMR (400 MHz, CDCl$_3$): δ7.65-7.59 (m, 2H), 7.53 (s, 1H), 4.96 (s, 1H), 4.78-4.71 (m, 1H), 1.60 (d, J=6.8 Hz, 3H). $^{13}$C NMR (100 MHz, CDCl$_3$): δ143.8, 134.6, 132.5, 127.8, 127.2, 122.5, 52.91, 21.15. IR (neat, cm$^{-1}$): 3268, 2966, 2924, 2871, 1727, 1572, 1459, 1389, 1320, 1284, 1193, 1165, 1138, 1073. HRMS (ESI): Calcd. for C$_8$H$_{12}$N$_2$O$_2$SBr ([M+NH$_4$]$^+$) m/z 278.97974, Found 278.97988.

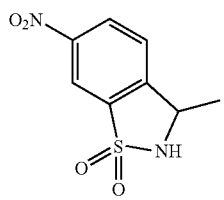

2i (Table 2, Entry 9) was synthesized by the general procedure from 2-ethyl-5-nitrobenzene-1-sulfonyl azide (1i) as a tan solid in 99% yield (45.2 mg). $^1$H
NMR (400 MHz, CDCl$_3$): δ8.60 (d, J=1.6 Hz, 1H), 8.49 (dd, J=8.4, 2.0 Hz, 1H), 7.60 (d, J=8.4 Hz, 1H) 4.91 (s, 1H), 4.87 (m, 1H), 1.69 (d, J=6.4 Hz, 3H). $^{13}$C NMR (100 MHz, CDCl$_3$): δ148.5, 147.7, 137.5, 128.1, 125.3, 117.4, 53.32, 21.40. IR (neat, cm$^{-1}$): 3243, 1600, 1529, 1351, 1282, 1162, 1137, 1094, 1049, 1025. HRMS (ESI): Calcd. for C$_8$H$_{12}$N$_3$O$_4$S ([M+NH$_4$]$^+$) m/z 246.05430, Found 246.05436.

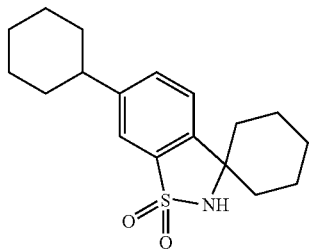

2j (Table 2, Entry 10) was synthesized by the general procedure from 2,5-dicyclohexylbenzene-1-sulfonyl azide (1j) as a tan solid in 87% yield (55.4 mg). $^1$H NMR (400 MHz, CDCl$_3$): δ7.53 (s, 1H), 7.42 (dd, J=8.0, 1.2 Hz, 1H), 7.25 (d, J=8.0 Hz, 1H), 4.67 (s, 1H), 2.59-2.46 (m, 1H), 1.85-1.73 (m, 12H), 1.63-1.53 (m, 2H), 1.44-1.21 (m, 6H). $^{13}$C NMR (100 MHz, CDCl$_3$): δ149.8, 143.6, 135.3, 132.3, 122.7, 118.9, 63.47, 44.24, 37.75, 34.21, 26.63, 25.89, 24.78, 22.55. IR (neat, cm$^{-1}$): 3268, 2928, 2851, 1728, 1447, 1384, 1296, 1268, 1164, 1137, 1072. HRMS (ESI): Calcd. for C$_{18}$H$_{26}$NO$_2$S ([M+H]$^+$) m/z 320.16788, Found 320.16886.

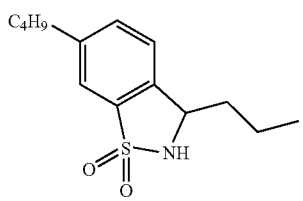

2k (Table 3, Entries 1-3) was synthesized by the general procedure from 2,5-dibutylbenzene-1-sulfonyl azide (1k) as tan oil. $^1$H NMR (400 MHz, CDCl$_3$): δ7.56 (s, 1H), 7.41 (d, J=8.0 Hz, 1H), 7.27 (d, J=7.6 Hz, 1 H) 4.66-4.60 (m, 2H), 2.70 (t, J=7.6 Hz, 2H), 1.95-1.90 (m, 1 H), 1.77-1.70 (m, 1 H), 1.62 (m, 2H), 1.52-1.44 (m, 2H), 1.36 (sext, J=7.2 Hz, 2H), 0.98 (t, J=7.2 Hz, 3H), 0.95 (t, J=7.2 Hz, 3H). $^{13}$C NMR (125 MHz, CDCl$_3$): δ144.8, 137.9, 135.5, 133.6, 123.7, 120.5, 57.51, 37.69, 35.23, 33.23, 22.19, 13.82, 13.71. IR (neat, cm$^{-1}$): 3259, 2958, 2931, 2872, 1489, 1465, 1381, 1287, 1152, 1107. HRMS (ESI): Calcd. for C$_{14}$H$_{22}$NO$_2$S ([M+H]$^+$) m/z 268.13658, Found 268.13665. Extensive efforts were made to attempt the separation of the 5-membered from 6-membered ring products. However, we were only able to isolate a small fraction of the pure 5-membered ring products in both of the cases, which allowed for NMR assignments and determination of the 5- to 6-membered ring product ratios by integration from $^1$H NMR spectra of 5- and 6-membered ring product mixtures.

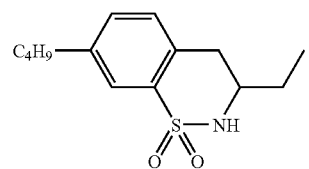

3k (Table 3, Entries 1-3) was synthesized by the general procedure from 2,5-dibutylbenzene-1-sulfonyl azide (1k) as tan oil. $^1$H NMR (400 MHz, CDCl$_3$): δ7.61 (s, 1H), 7.25-7.23 (m, 1H), 7.10 (d, J=8.0 Hz, 1H), 4.17 (d, J=11.6 Hz, 1H), 3.82-3.73 (m, 1H), 2.91 (dd, J=16.8, 4.0 Hz, 1H), 2.76-2.72 (m, 1H), 2.61 (t, J=8.0 Hz, 2H), 1.70-1.64 (m, 2H), 1.62-1.55 (m, 2H), 1.36-1.30 (m, 2H), 1.05 (t, J=7.2 Hz, 3H), 0.90 (t, J=7.2 Hz, 3H). Extensive efforts were made to attempt the separation of the 5-membered from 6-membered ring products. However, we were only able to isolate a small fraction of the pure 5-membered ring products in both of the cases, which allowed for NMR assignments and determination of the 5- to 6-membered ring product ratios by integration from $^1$H NMR spectra of 5- and 6-membered ring product mixtures.

2l (Table 3, Entries 4-9) was synthesized by the general procedure from 2,5-dipropylbenzene-1-sulfonyl azide (1l) as tan oil. $^1$H NMR (400 MHz, CDCl$_3$): δ7.57 (s, 1H), 7.42 (d, J=8.0 Hz, 1H), 7.27 (d, J=8.4 Hz, 1H), 4.62 (m, 2H), 2.68 (t, J=7.6 Hz, 2H), 2.05-2.00 (m, 1H), 1.83-1.78 (m, 1H), 1.67 (sext, J=7.6 Hz, 2H), 1.03 (t, J=7.2 Hz, 3H), 0.95 (t, J=7.2 Hz, 3H). $^{13}$C NMR (125 MHz, CDCl$_3$): δ144.6, 137.5, 135.7, 133.6, 123.7, 120.6, 58.85, 37.56, 28.72, 24.22, 13.66, 9.88. IR (neat, cm$^{-1}$): 3272, 2964, 2931, 2872, 1489, 1458, 1379, 1281, 1151, 1094, 1049. HRMS (ESI): Calcd. for C$_{12}$H$_{18}$NO$_2$S ([M+H]$^+$) m/z 240.10528, Found 240.10521. Extensive efforts were made to attempt the separation of the 5-membered from 6-membered ring products. However, we were only able to isolate a small fraction of the pure 5-membered ring products in both of the cases, which allowed for NMR assignments and determination of the 5- to 6-membered ring product ratios by integration from $^1$H NMR spectra of 5- and 6-membered ring product mixtures

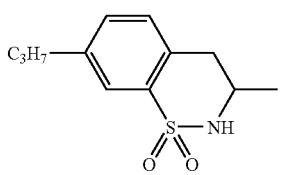

3l (Table 3, Entries 4-9) was synthesized by the general procedure from 2,5-dipropylbenzene-1-sulfonyl azide (1l) as tan oil. $^1$H NMR (400 MHz, CDCl$_3$): δ7.59 (s, 1H), 7.25-7.20 (m, 1H), 7.07 (d, J=8.0 Hz, 1H), 4.41 (d, J=11.2 Hz 1H), 4.03-3.94 (m, 1H), 2.89 (dd, J=17.2, 3.6 Hz, 1H), 2.72 (dd, J=17.2, 11.2Hz, 1H), 2.57 (t, J=7.6 Hz, 2H), 1.69-1.59 (m, 2H), 1.35 (d, J=6.8 Hz, 3H), 0.92 (t, J=7.2 Hz, 3H). Extensive efforts were made to attempt the separation of the 5-membered from 6-membered ring products. However, we were only able to isolate a small fraction of the pure 5-membered ring products in both of the cases, which allowed for NMR assignments and determination of the 5- to 6-membered ring product ratios by integration from $^1$H NMR spectra of 5- and 6-membered ring product mixtures.

EXAMPLE 2

Except as noted below, the procedures of Example 1 were repeated for 2l and 3l with different cobalt complexes to demonstrate the influence of different cobalt porphyrin complexes upon regioselectivity and stereoselectivity. The results are presented in Table 4 and the structures for the porphyrin complexes referenced in Table 4 appear in Table 5.

TABLE 4

| Entry[a] | [Co(Por)][b] | distribution[c] | Yield (%)[d] | % ee[e] |
|---|---|---|---|---|
| 1 | [Co(3,5-ditBuChenPhyrin)] | 67:33 | 98% | 5: 21% ee<br>6: 39% ee |
| 2 | [(Co(2,6-diMeORuppelPhyrin)] | 71:29 | 61% | 5: 41% ee<br>6: 10% ee |
| 3 | [Co(2,6-diMeOZhuPhyrin)] | 82:18 | 19% | 5: 75% ee<br>6: 44% ee |
| 4 | [Co(Por1)] | 82:18 | 99% | — |
| 5 | [Co(Cor1)PPh$_3$] | 85:15 | 93% | — |
| 6 | [Co(Por2)] | 54:46 | 45% | — |
| 7 | [Co(Cor2)PPh$_3$] | 35:65 | 96% | — |
| 8 | [Co(Cor3)PPh$_3$] | 30:70 | 96% | — |

[a]Performed in C$_6$H$_5$Cl for 18 h under N$_2$ with 2 mol % [Co(Por/Cor)] in the presence of 5 Å MS; [azide]) 0.20 M.
[b]See below for structures.
[c]Ratio of 5- to 6-membered ring products determined by NMR.
[d]Combined isolated yields of 5- and 6-membered ring products.

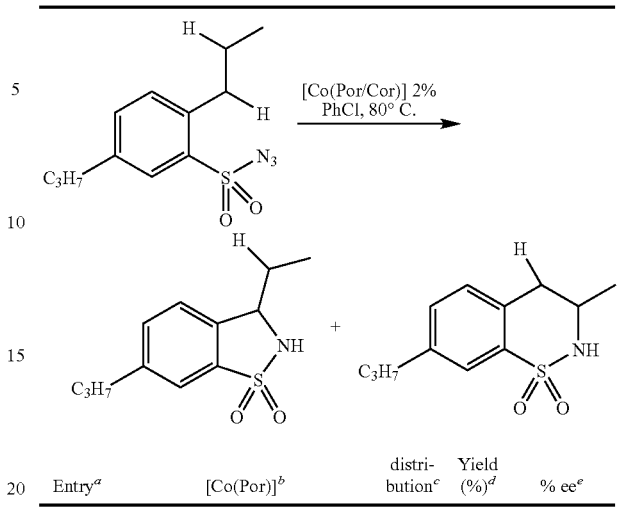

TABLE 4-continued

[e]Determined by HPLC utilizing a WhelkO-1 column eltuing 98% hexanes and 2% isopropanol at 1.0 ml/min.

TABLE 5

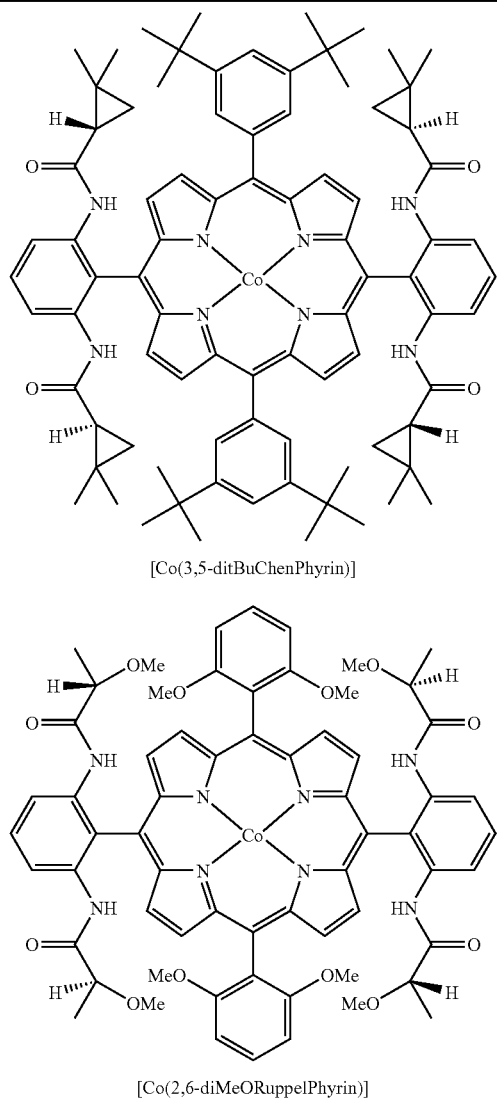

[Co(3,5-ditBuChenPhyrin)]

[Co(2,6-diMeORuppelPhyrin)]

TABLE 5-continued
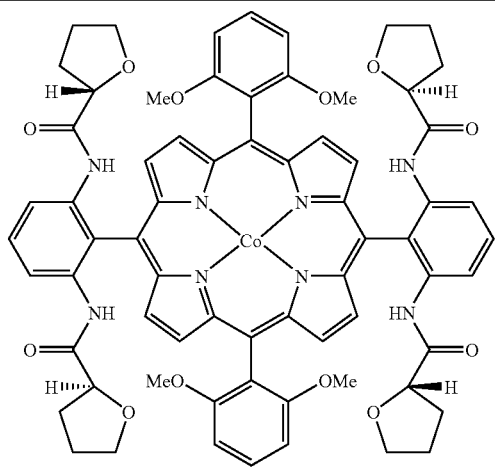
[Co(2,6-diMeOZhuPhyrin)]
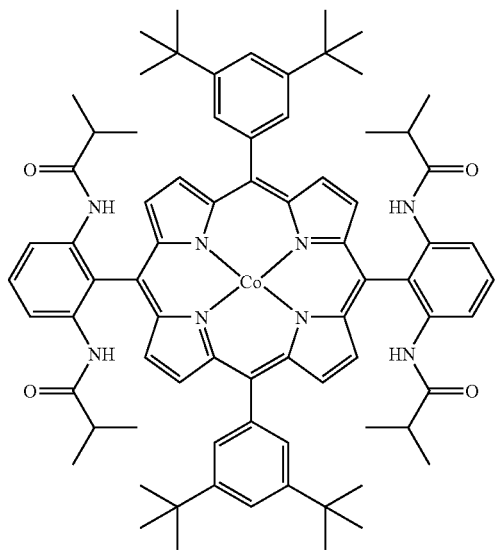
[Co(Por1)]
TABLE 5-continued
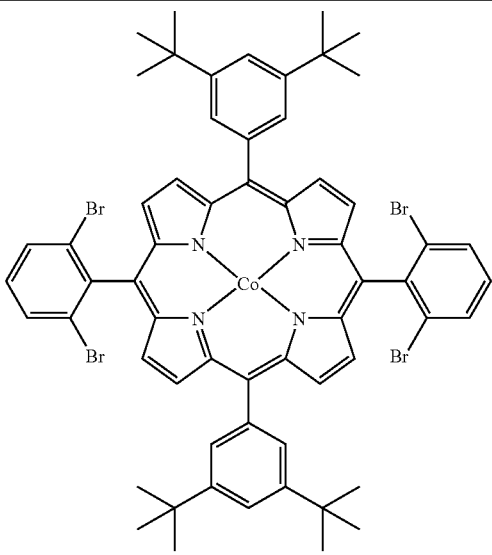
[Co(Por2)]
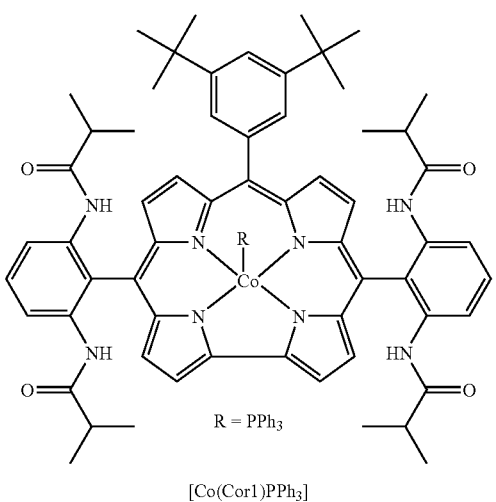
R = PPh$_3$
[Co(Cor1)PPh$_3$]
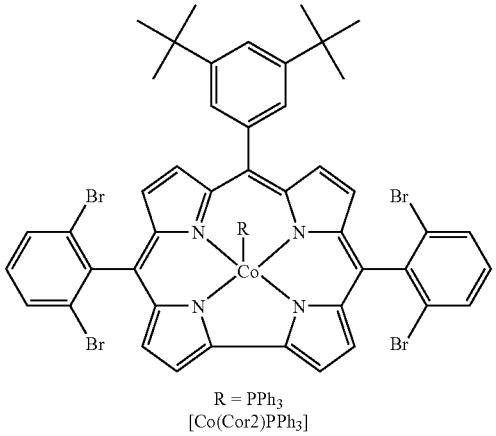
R = PPh$_3$
[Co(Cor2)PPh$_3$]

TABLE 5-continued

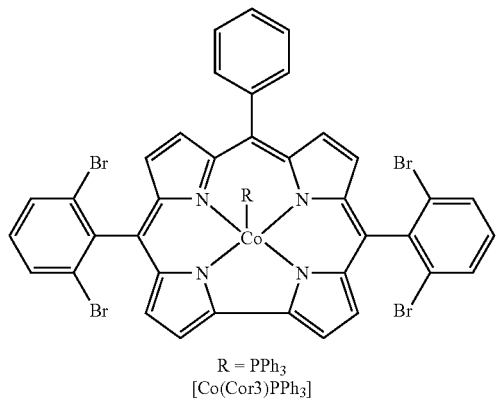

R = PPh₃
[Co(Cor3)PPh₃]

What is claimed is:

1. A process for the preparation of a sultam, the process comprising treating a sulfonylazide with an asymmetric cobalt (II) porphyrin complex to catalyze the amination of a C—H bond to form the sultam, the sulfonylazide corresponding to Formula 9a and the sultam corresponding to Formula 9

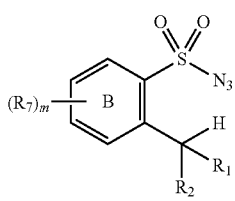

Formula 9a

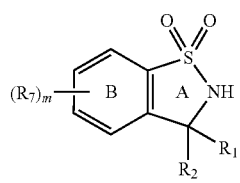

Formula 9 wherein $R_1$ and $R_2$ are independently hydrogen, hydrocarbyl, substituted hydrocarbyl, halo, hydroxyl, alkoxyl, or heterocyclo, each $R_7$ is independently hydrocarbyl, substituted hydrocarbyl, halo, nitro, alkoxyl, hydroxyl, acyl, acyloxy, or heterocyclo, and m is 0 to 4.

2. The process of claim 1 wherein m is 1 to 4 and each $R_7$ is independently alkyl, halo, alkoxyl, hydroxyl, or nitro.

3. The process of claim 1 wherein m is 1 to 4 and each $R_7$ is independently alkyl, substituted alkyl, halo or nitro.

4. The process of claim 1 wherein m is 1 to 4 and each $R_7$ is independently alkyl.

5. The process of claim 1 wherein one of $R_1$ and $R_2$ is hydrogen and the other is hydrocarbyl, substituted hydrocarbyl, halo, hydroxyl, alkoxyl, or heterocyclo.

6. The process of claim 1 wherein $R_1$ is hydrogen and $R_2$ is alkyl, aryl, or heterocyclo.

7. The process of claim 1 wherein m is 1 to 4, each $R_7$ is independently alkyl, halo, alkoxyl, hydroxyl, or nitro, and $R_1$ and $R_2$ are hydrogen.

8. The process of claim 1 wherein m is 1 to 4, each $R_7$ is independently alkyl, halo, alkoxyl, hydroxyl, or nitro, one of $R_1$ and $R_2$ is hydrogen, and the other of $R_1$ and $R_2$ is hydrocarbyl, substituted hydrocarbyl, halo, hydroxyl, alkoxyl, or heterocyclo.

9. The process of claim 1 wherein the metal porphyrin complex is a metal porphyrin complex corresponding to Formula Co(3,5-ditBuChenPhyrin), Formula Co(2,6-diMeORuppelPhyrin), Formula Co(2,6-diMeOZhuPhyrin), Formula Co(Por1), Formula Co(Por2), Formula Co(Cor1)PPh₃, Formula Co(Cor2)PPh₃ or Formula Co(Cor1)PPh₃:

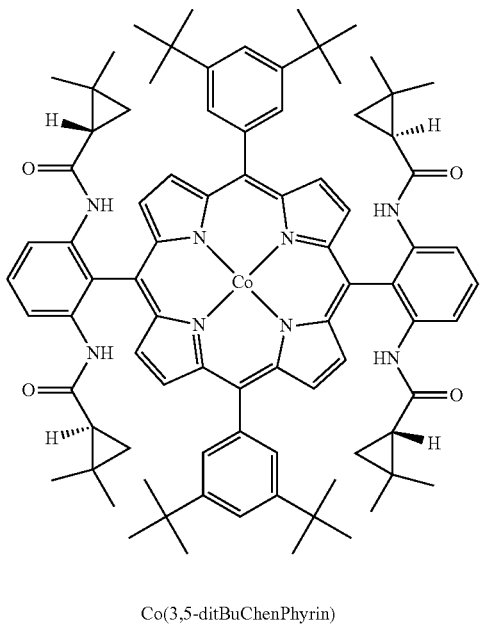

Co(3,5-ditBuChenPhyrin)

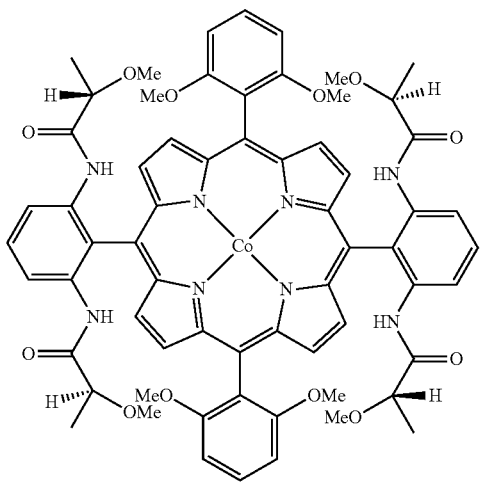

Co(2,6-diMeORuppelPhyrin)

-continued
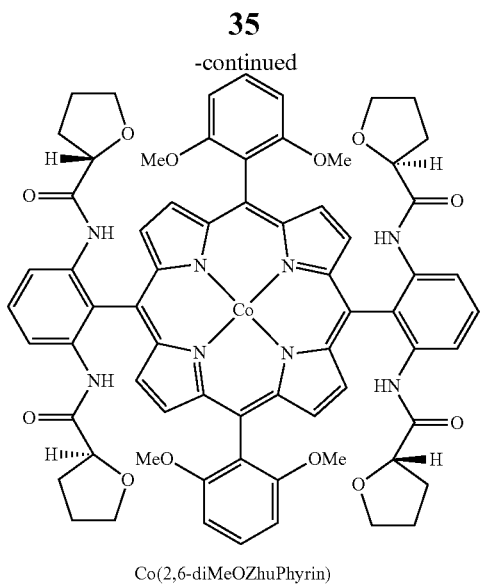
Co(2,6-diMeOZhuPhyrin)
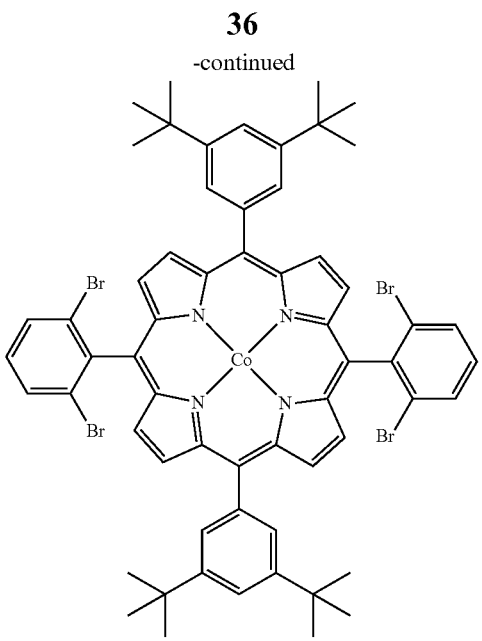
Co(Por2)
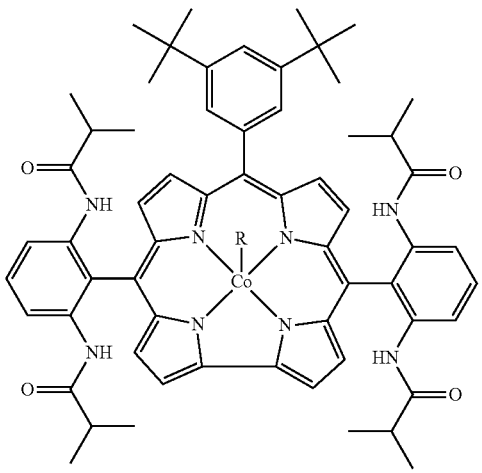
Co(Cor1)PPh$_3$
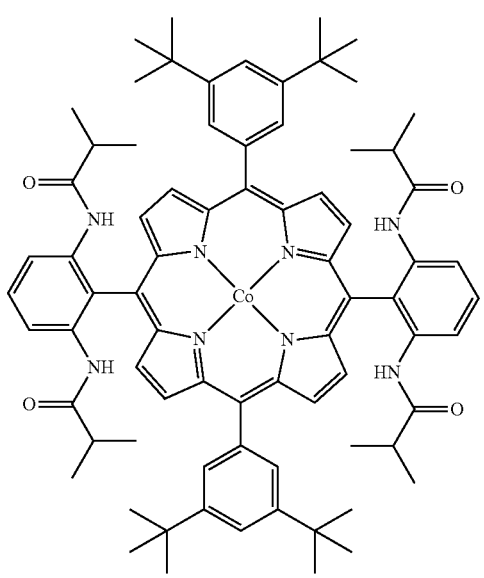
Co(Por1)
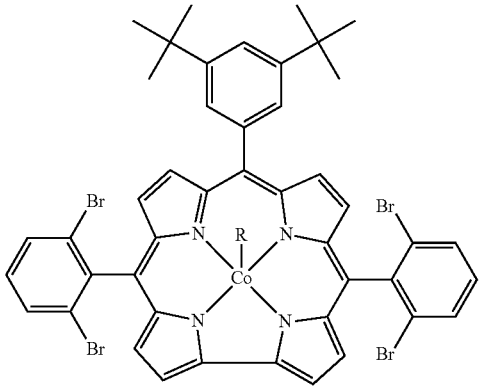
Co(Cor2)PPh$_3$ -continued

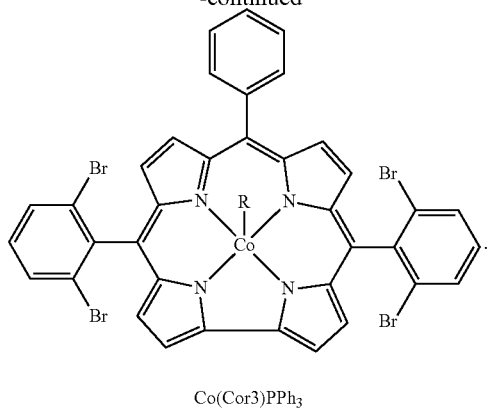

Co(Cor3)PPh₃

R = PPh₃

10. The process of claim 2 wherein the metal porphyrin complex is a metal porphyrin complex corresponding to Formula Co(3,5-ditBuChenPhyrin), Formula Co(2,6-diMeORuppelPhyrin), Formula Co(2,6-diMeOZhuPhyrin), Formula Co(Por1), Formula Co(Por2), Formula Co(Cor1)PPh₃, Formula Co(Cor2)PPh₃ or Formula Co(Cor1)PPh₃:

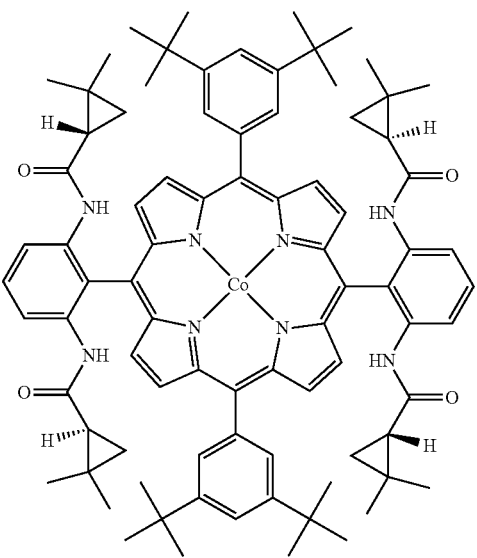

Co(3,5-ditBuChenPhyrin)

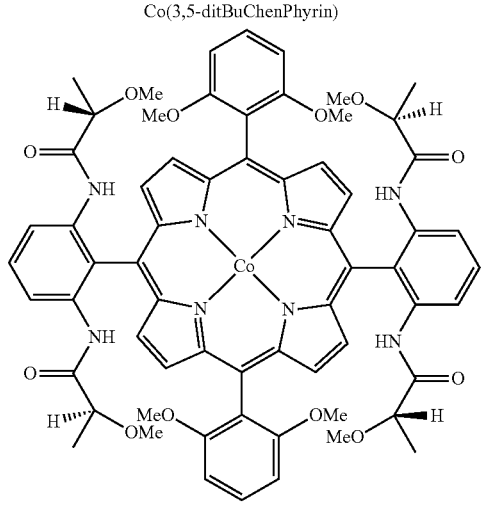

Co(2,6-diMeORuppelPhyrin)

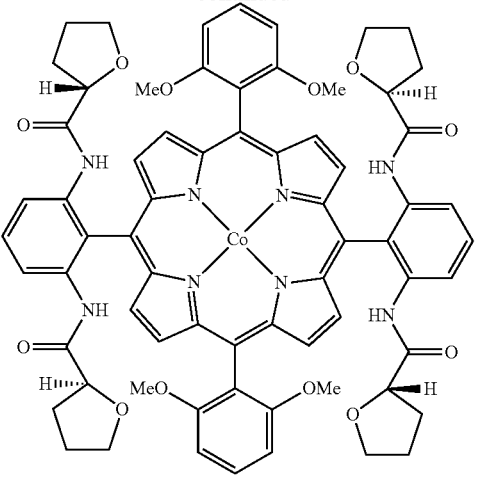

Co(2,6-diMeOZhuPhyrin)

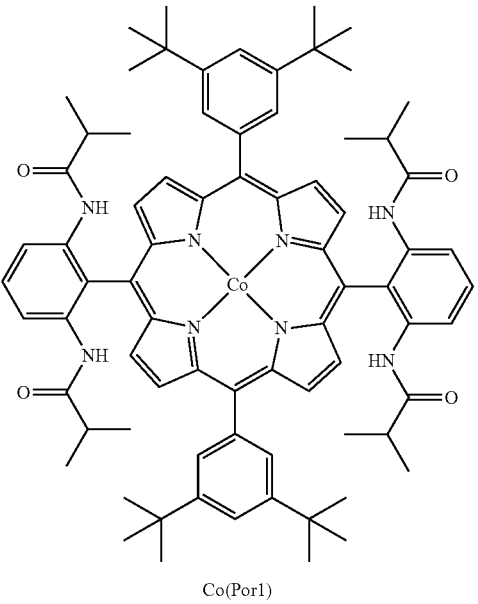

Co(Por1)

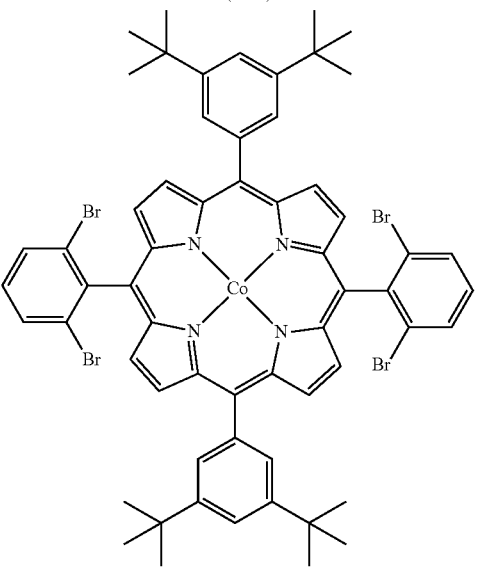

Co(Por2)

-continued

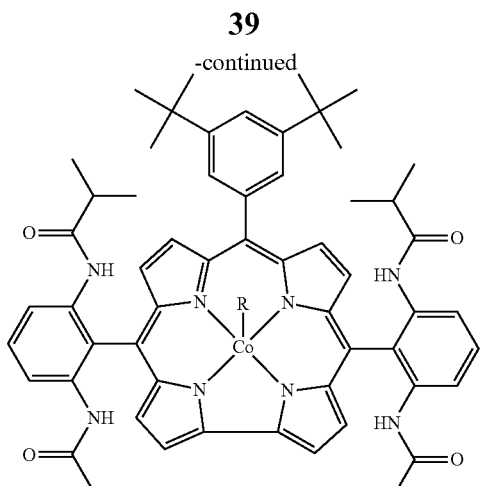

Co(Cor1)PPh₃

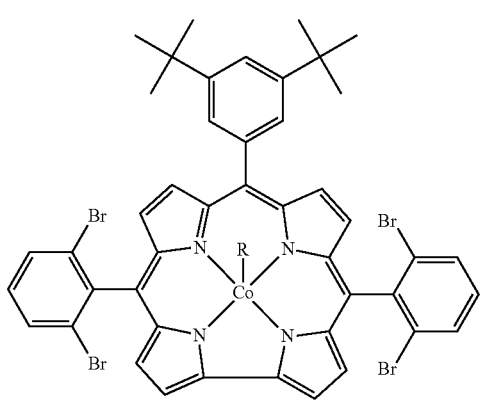

Co(Cor2)PPh₃

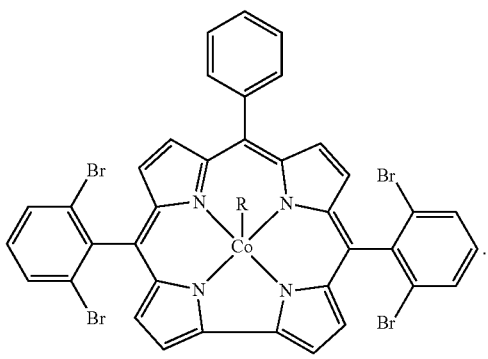

Co(Cor3)PPh₃

R = PPh₃

11. The process of claim 3 wherein the metal porphyrin complex is a metal porphyrin complex corresponding to Formula Co(3,5-ditBuChenPhyrin), Formula Co(2,6-diMeORuppelPhyrin), Formula Co(2,6-diMeOZhuPhyrin), Formula Co(Por1), Formula Co(Por2), Formula Co(Cor1)PPh₃, Formula Co(Cor2)PPh₃ or Formula Co(Cor1)PPh₃:

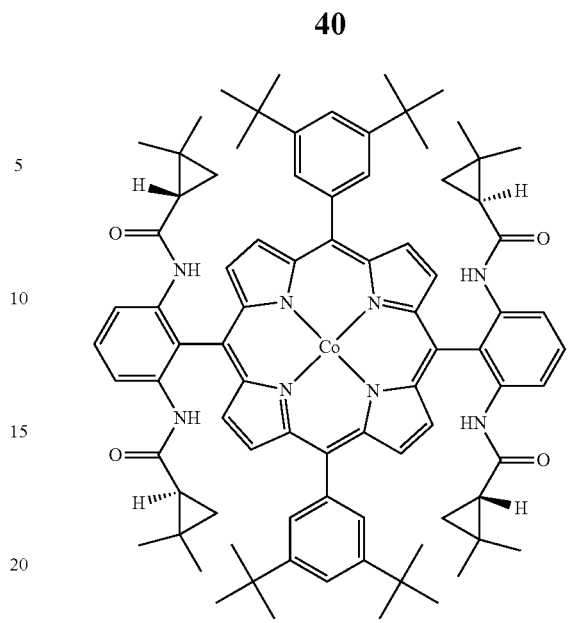

Co(3,5-ditBuChenPhyrin)

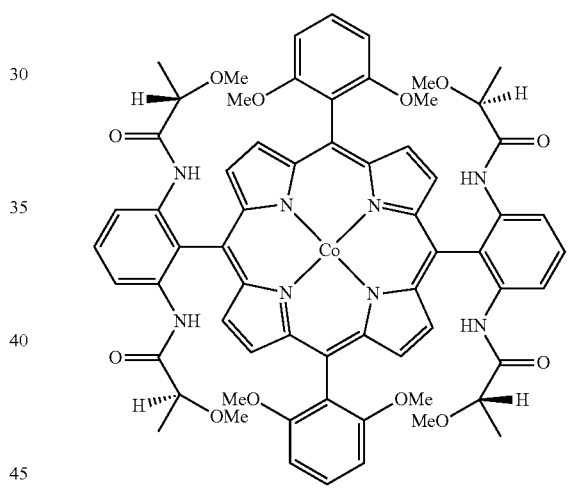

Co(2,6-diMeORuppelPhyrin)

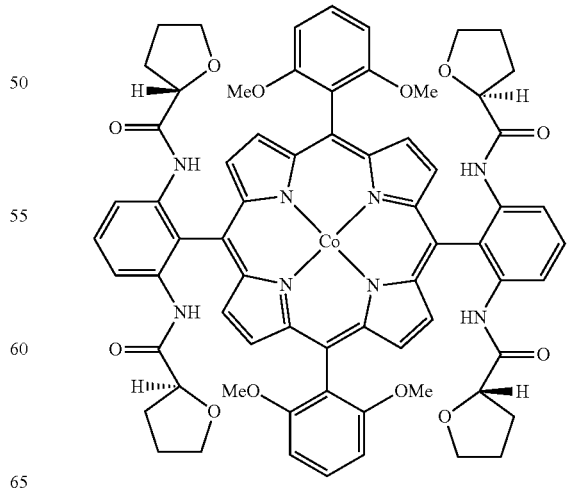

Co(2,6-diMeOZhuPhyrin)

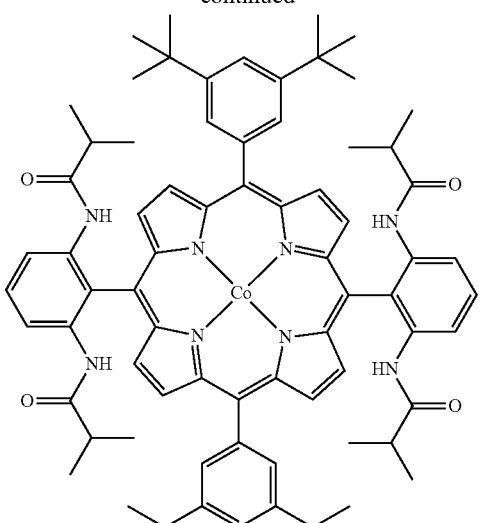
Co(Por1)
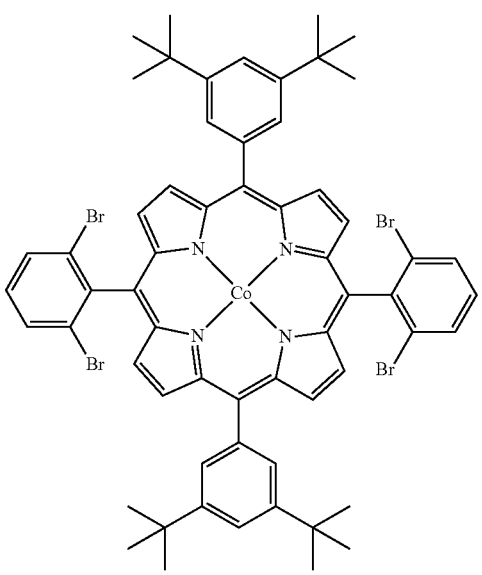
Co(Por2)
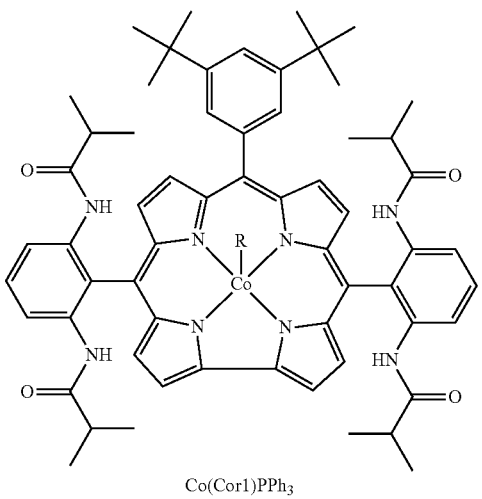
Co(Cor1)PPh₃
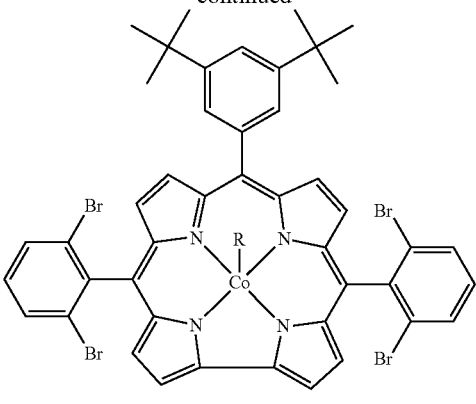
Co(Cor2)PPh₃
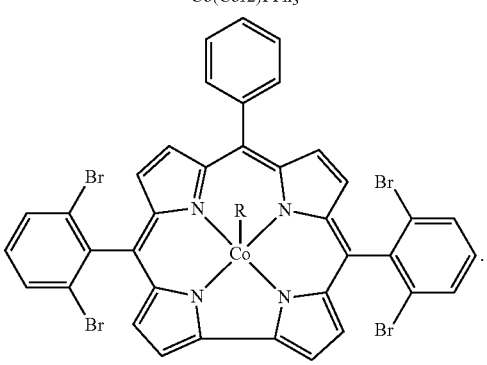
Co(Cor3)PPh₃
R = PPh₃
12. The process of claim 4 wherein the metal porphyrin complex is a metal porphyrin complex corresponding to Formula Co(3,5-ditBuChenPhyrin), Formula Co(2,6-diMeORuppelPhyrin), Formula Co(2,6-diMeOZhuPhyrin), Formula Co(Por1), Formula Co(Por2), Formula Co(Cor1)PPh₃, Formula Co(Cor2)PPh₃ or Formula Co(Cor1)PPh₃:
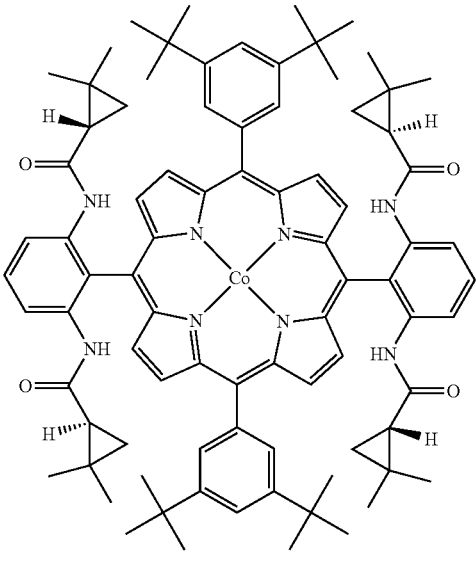
Co(3,5-ditBuChenPhyrin)

-continued
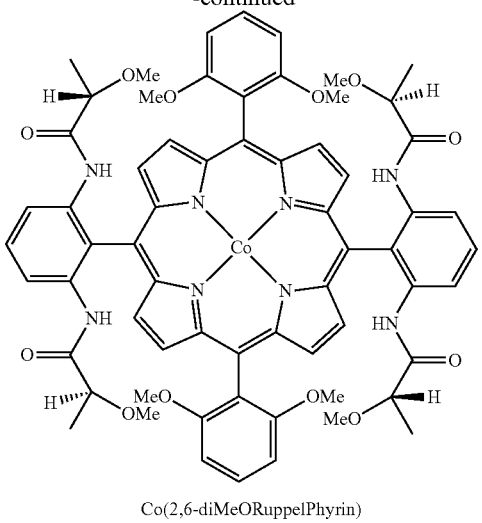
Co(2,6-diMeORuppelPhyrin)
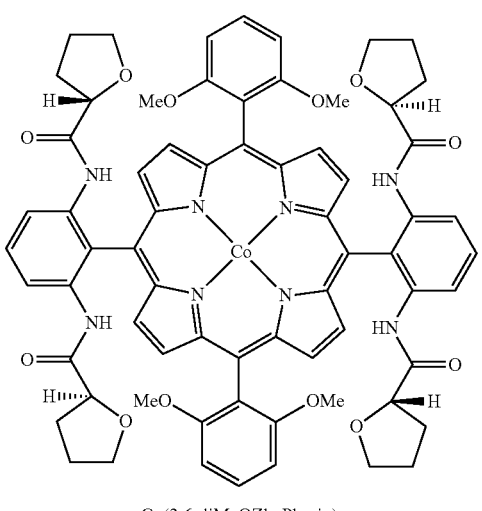
Co(2,6-diMeOZhuPhyrin)
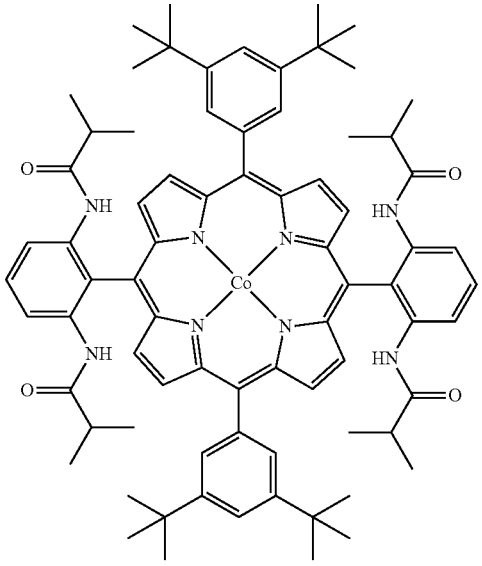
Co(Por1)
-continued
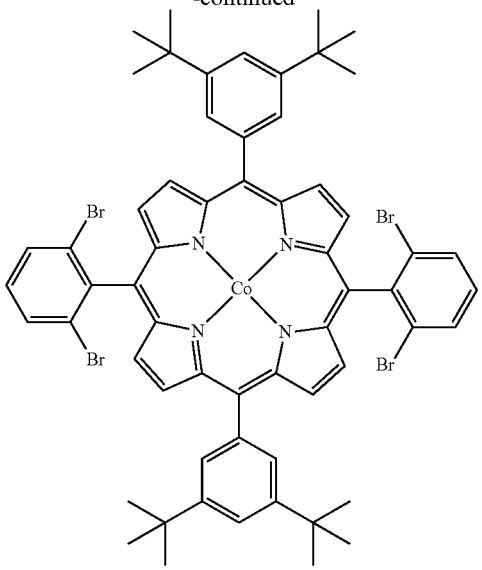
Co(Por2)
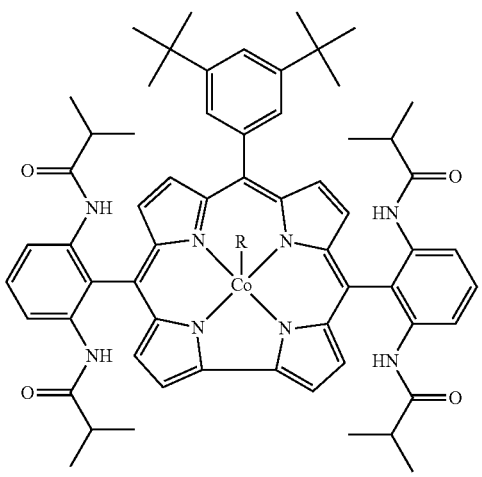
Co(Cor1)PPh₃
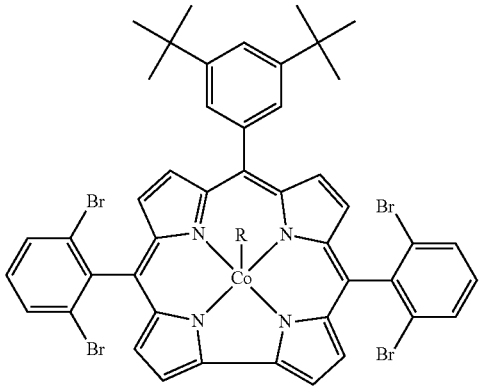
Co(Cor2)PPh₃

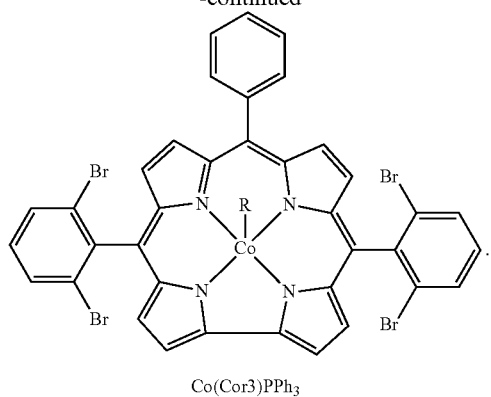

Co(Cor3)PPh₃

R = PPh₃

13. The process of claim 5 wherein the metal porphyrin complex is a metal porphyrin complex corresponding to Formula Co(3,5-ditBuChenPhyrin), Formula Co(2,6-diMeORuppelPhyrin), Formula Co(2,6-diMeOZhuPhyrin), Formula Co(Por1), Formula Co(Por2), Formula Co(Cor1)PPh₃, Formula Co(Cor2)PPh₃ or Formula Co(Cor1)PPh₃:

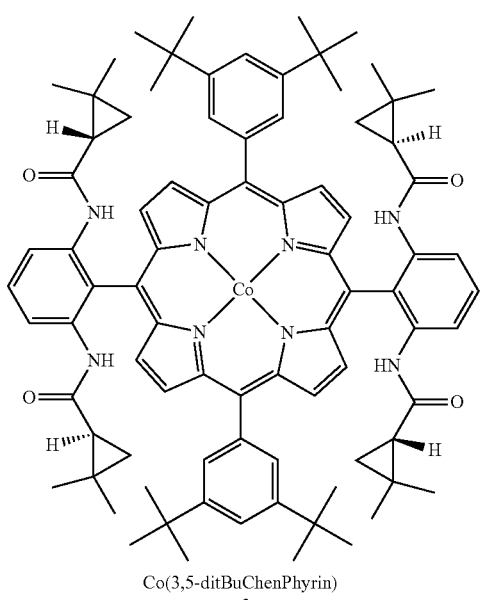

Co(3,5-ditBuChenPhyrin)

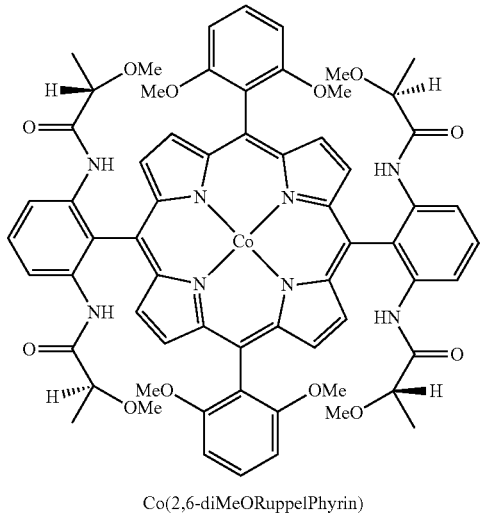

Co(2,6-diMeORuppelPhyrin)

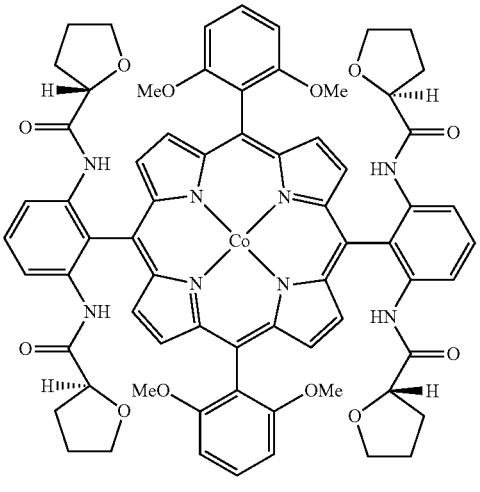

Co(2,6-diMeOZhuPhyrin)

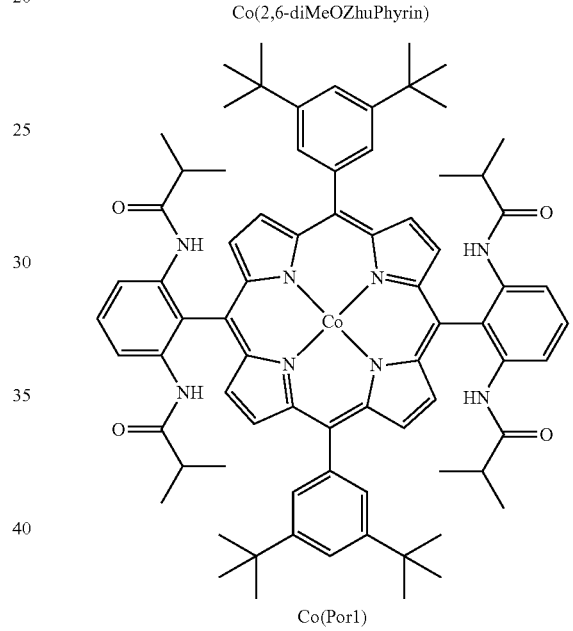

Co(Por1)

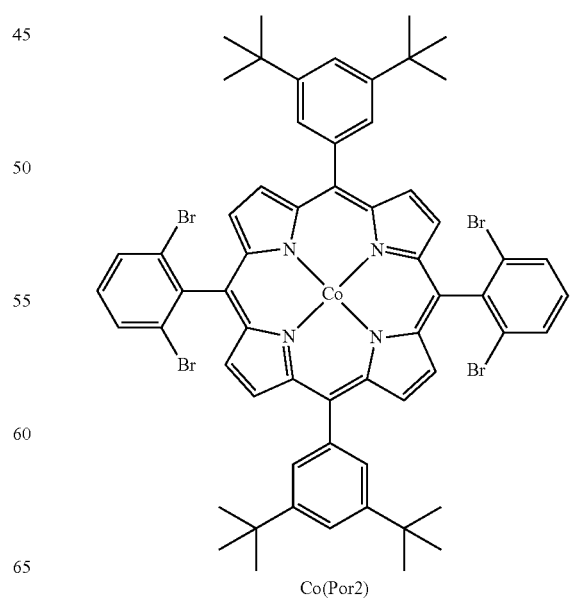

Co(Por2)

-continued

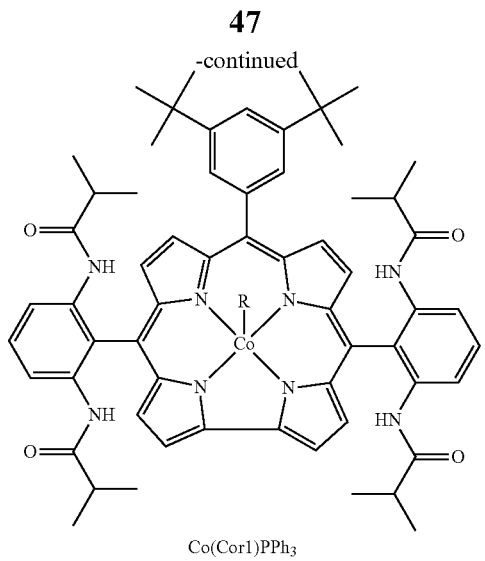
Co(Cor1)PPh₃

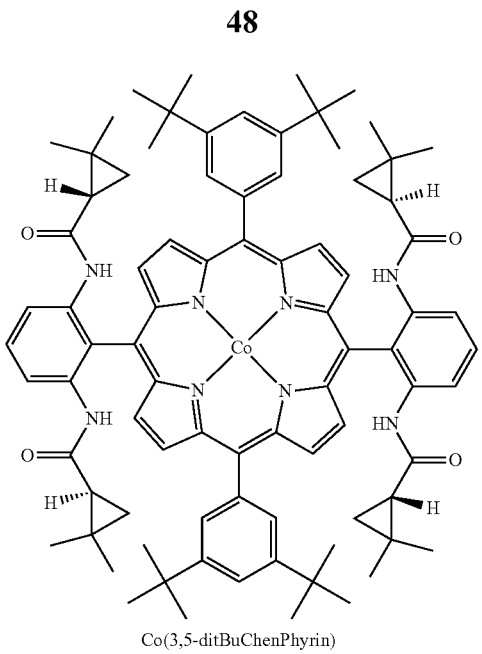
Co(3,5-ditBuChenPhyrin)

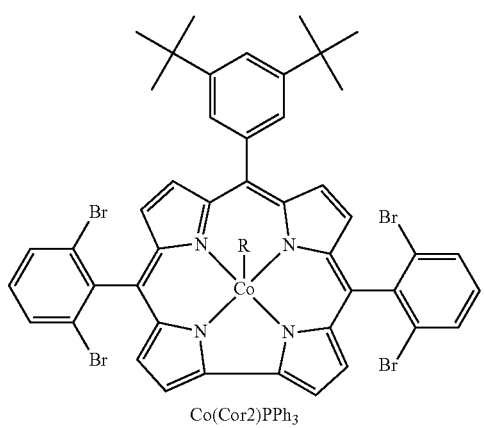
Co(Cor2)PPh₃

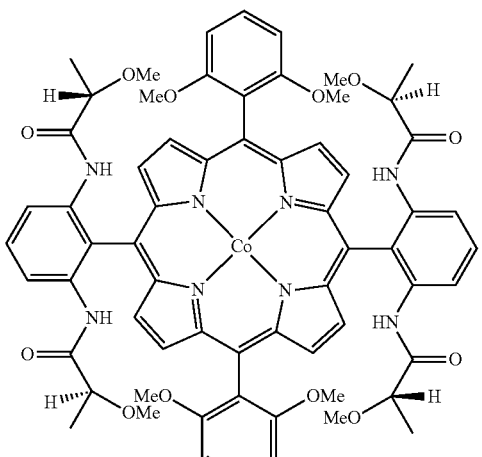
Co(2,6-diMeORuppelPhyrin)

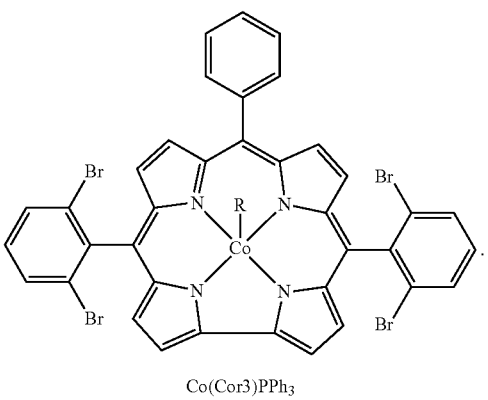
Co(Cor3)PPh₃

R = PPh₃

14. The process of claim 6 wherein the metal porphyrin complex is a metal porphyrin complex corresponding to Formula Co(3,5-ditBuChenPhyrin), Formula Co(2,6-diMeORuppelPhyrin), Formula Co(2,6-diMeOZhuPhyrin), Formula Co(Por1), Formula Co(Por2), Formula Co(Cor1)PPh₃, Formula Co(Cor2)PPh₃ or Formula Co(Cor1)PPh₃:

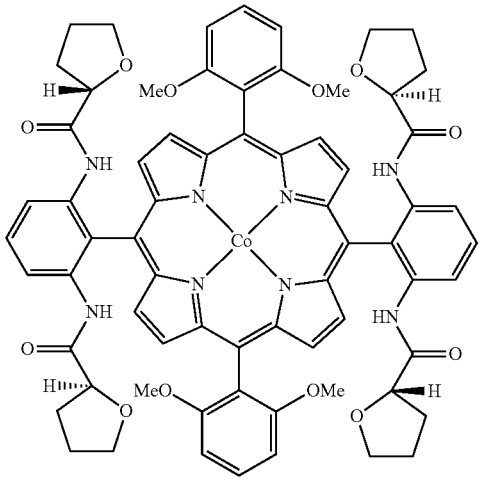
Co(2,6-diMeOZhuPhyrin)

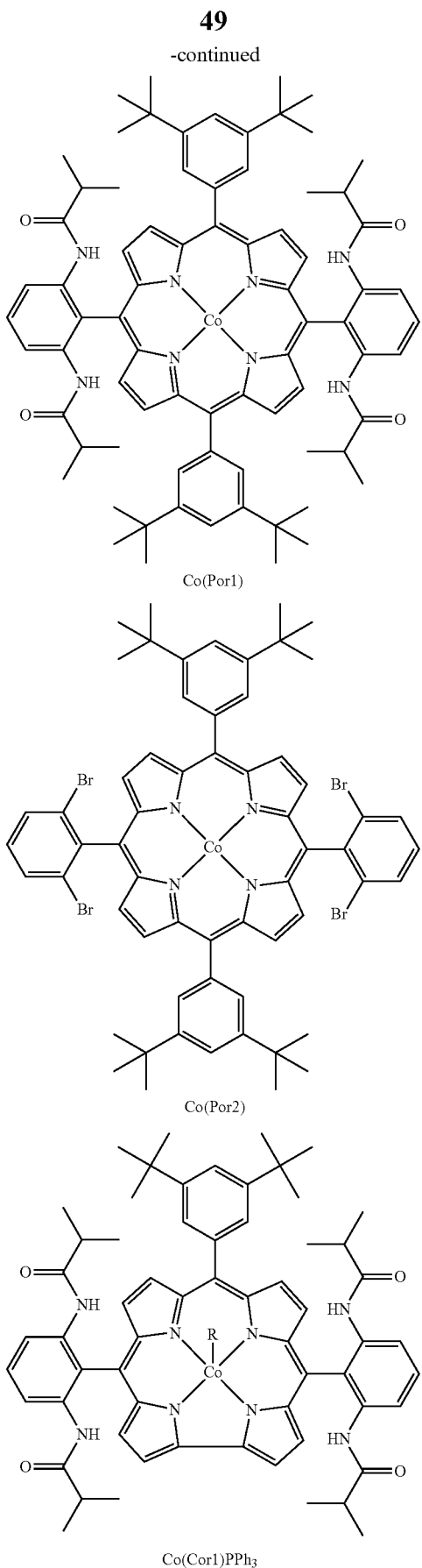
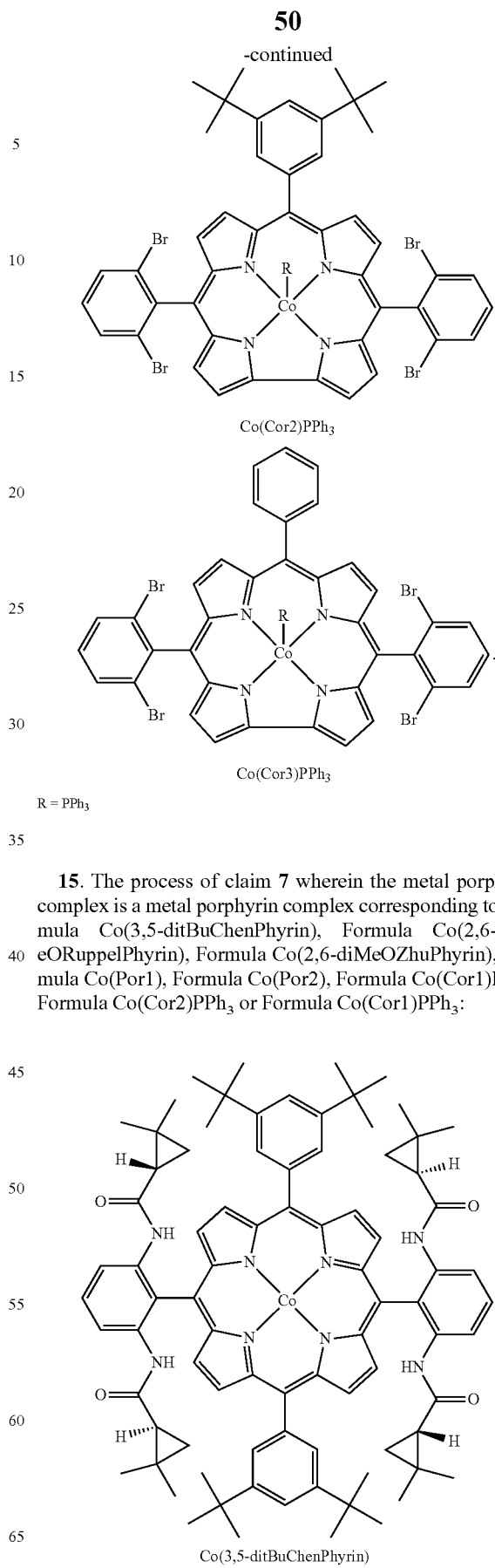
15. The process of claim 7 wherein the metal porphyrin complex is a metal porphyrin complex corresponding to Formula Co(3,5-ditBuChenPhyrin), Formula Co(2,6-diMeORuppelPhyrin), Formula Co(2,6-diMeOZhuPhyrin), Formula Co(Por1), Formula Co(Por2), Formula Co(Cor1)PPh₃, Formula Co(Cor2)PPh₃ or Formula Co(Cor1)PPh₃:

-continued
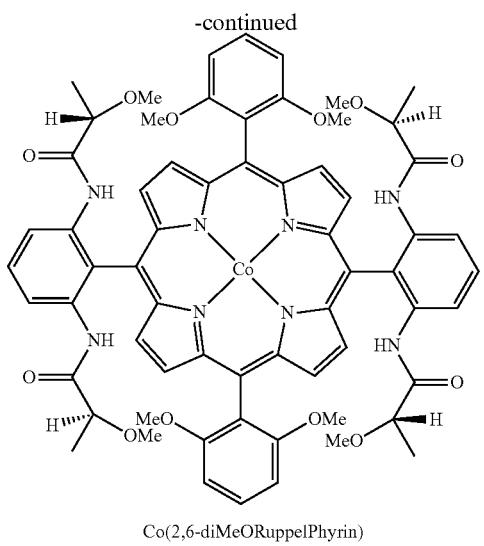
Co(2,6-diMeORuppelPhyrin)
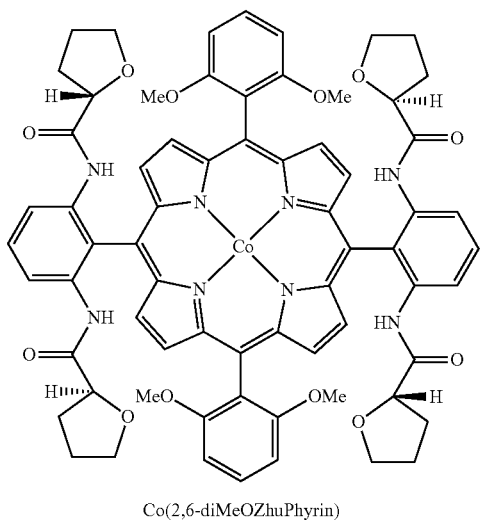
Co(2,6-diMeOZhuPhyrin)
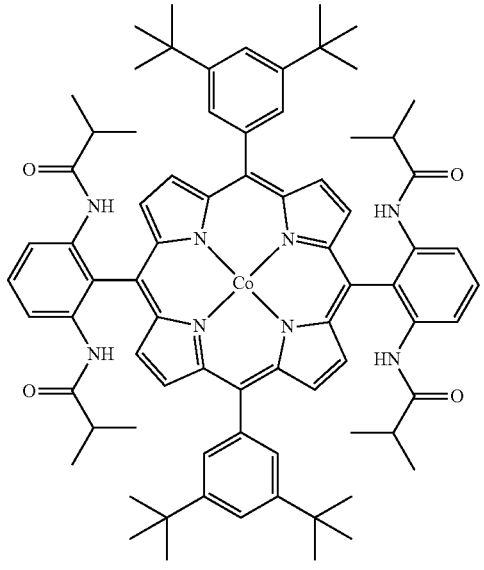
Co(Por1)
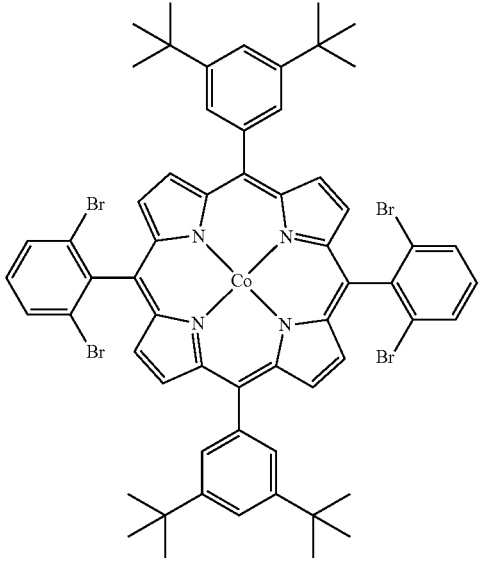
Co(Por2)
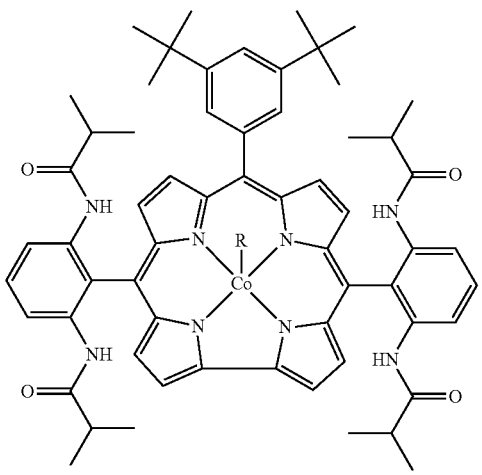
Co(Cor1)PPh$_3$
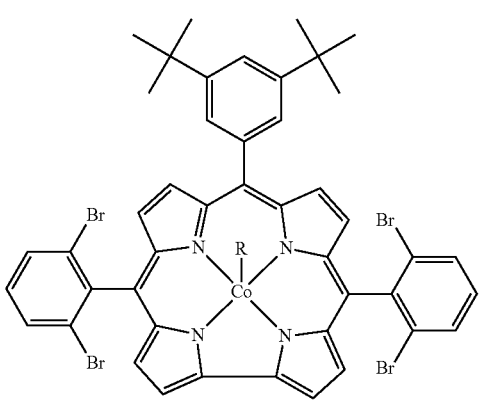
Co(Cor2)PPh$_3$

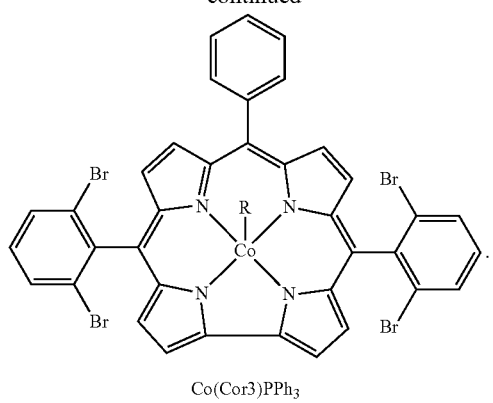

Co(Cor3)PPh₃

R = PPh₃

16. The process of claim 8 wherein the metal porphyrin complex is a metal porphyrin complex corresponding to Formula Co(3,5-ditBuChenPhyrin), Formula Co(2,6-diMeORuppelPhyrin), Formula Co(2,6-diMeOZhuPhyrin), Formula Co(Por1), Formula Co(Por2), Formula Co(Cor1)PPh₃, Formula Co(Cor2)PPh₃ or Formula Co(Cor1)PPh₃:

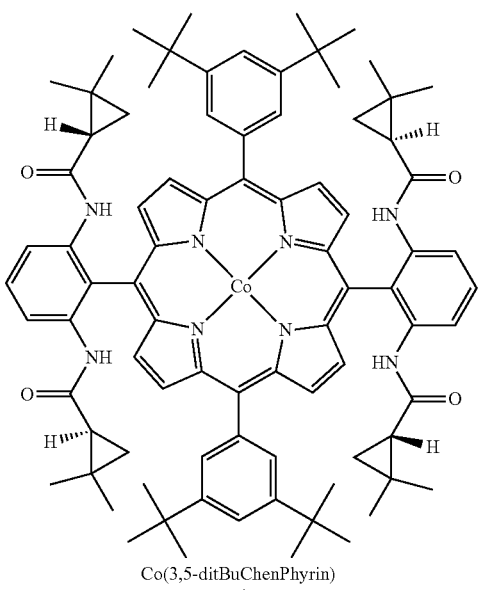

Co(3,5-ditBuChenPhyrin)

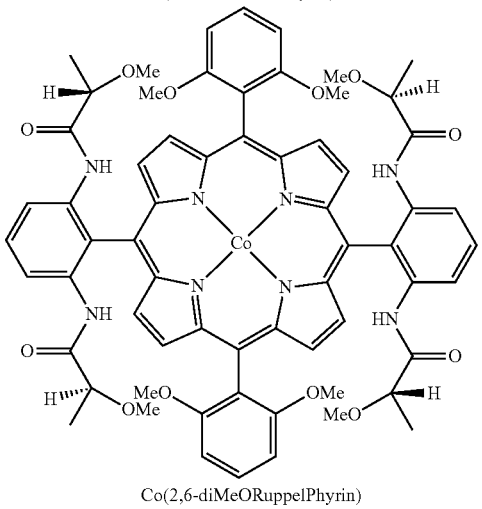

Co(2,6-diMeORuppelPhyrin)

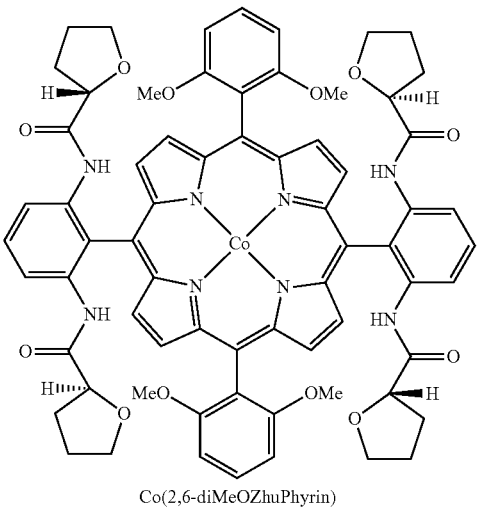

Co(2,6-diMeOZhuPhyrin)

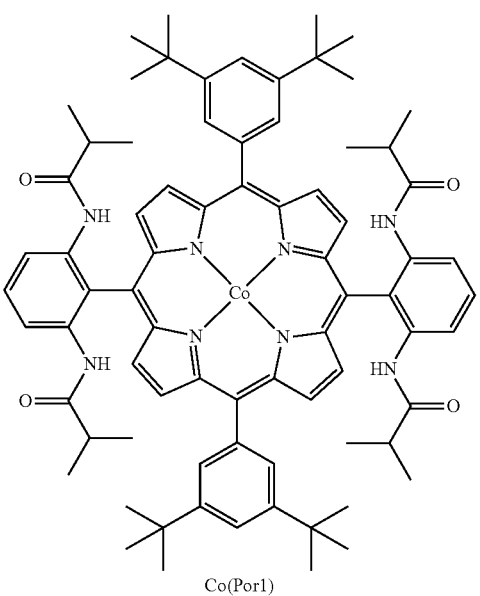

Co(Por1)

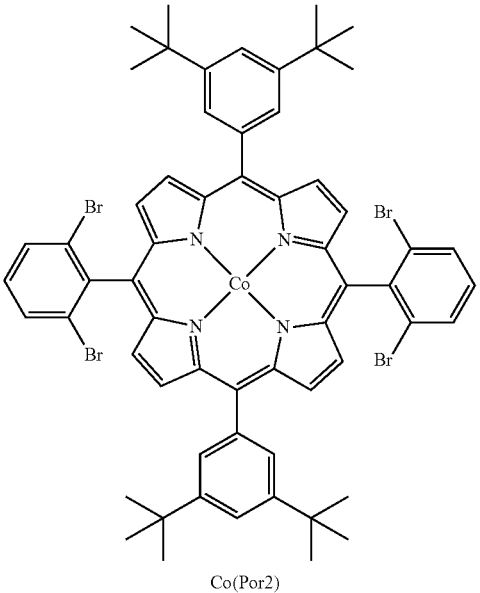

Co(Por2)

17. The process of claim 1 wherein the metal porphyrin complex is
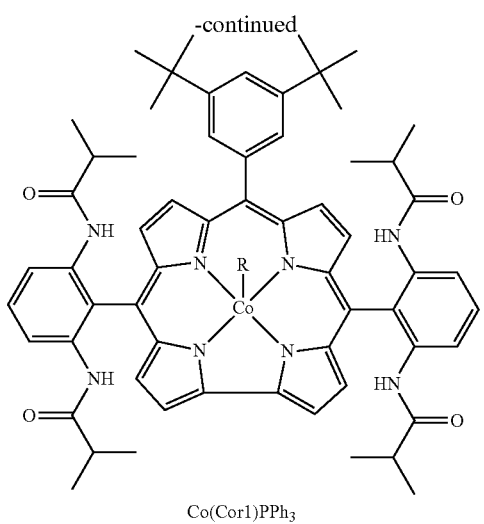
Co(Cor1)PPh₃
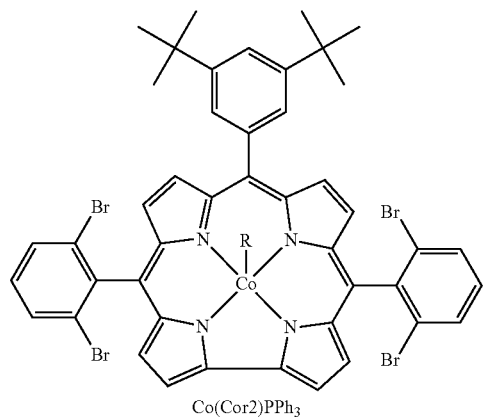
Co(Cor2)PPh₃
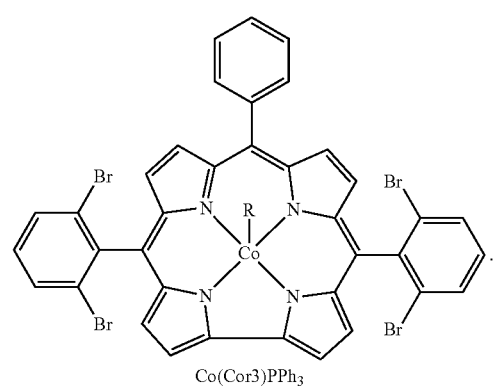
Co(Cor3)PPh₃
R = PPh₃
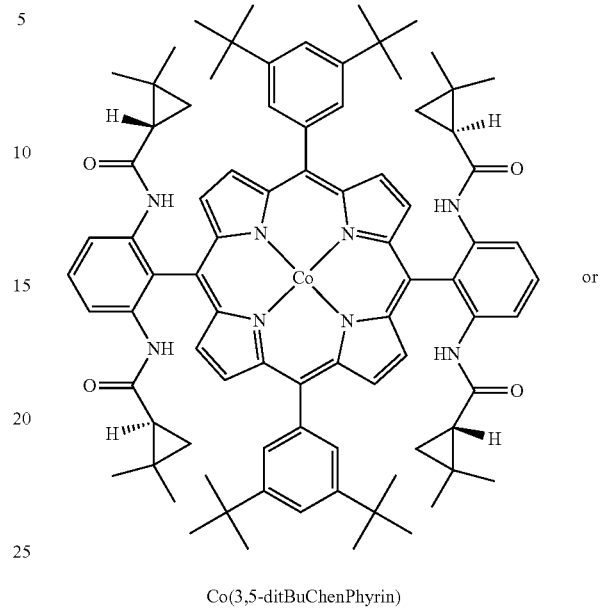
Co(3,5-ditBuChenPhyrin)
or
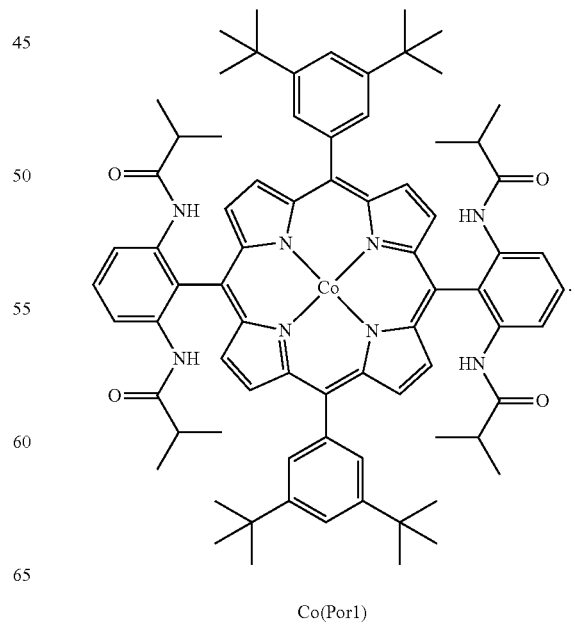
Co(Por1)

18. The process of claim 2 wherein the metal porphyrin complex is
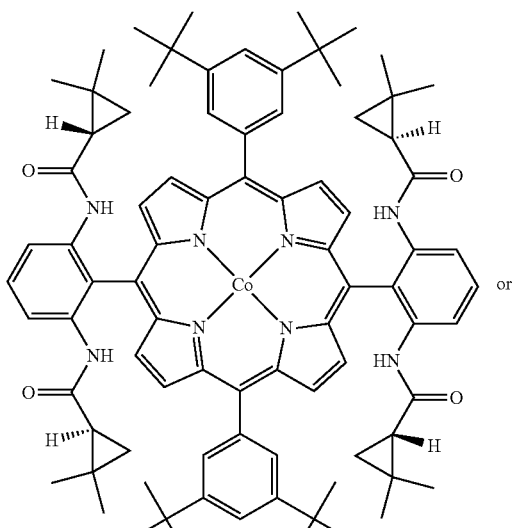
Co(3,5-ditBuChenPhyrin)
19. The process of claim 3 wherein the metal porphyrin complex is
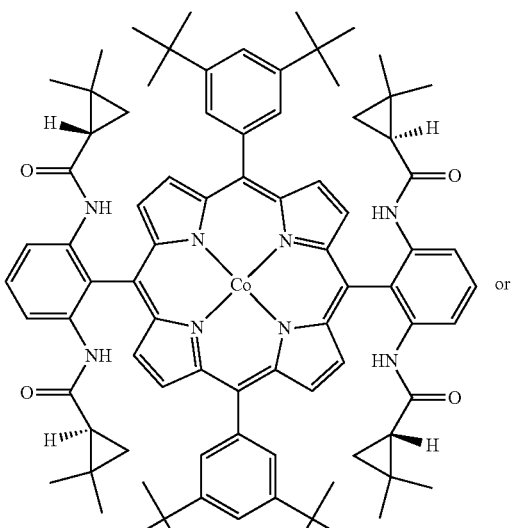
Co(3,5-ditBuChenPhyrin)
or
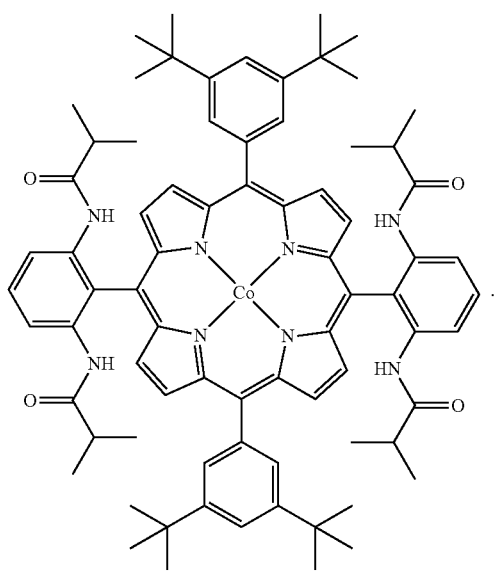
Co(Por1)
or
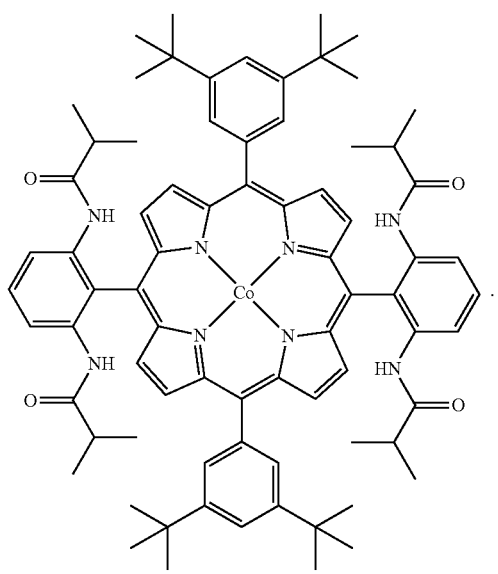
Co(Por1)

20. The process of claim 4 wherein the metal porphyrin complex is
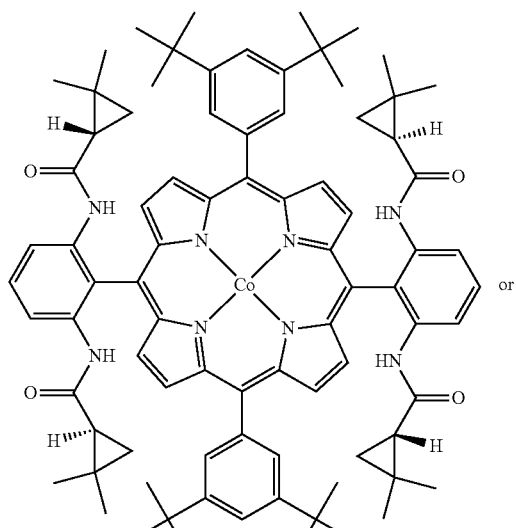
Co(3,5-ditBuChenPhyrin)
or
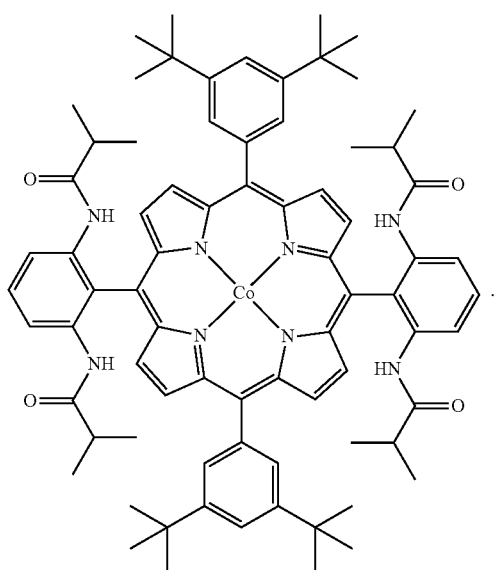
Co(Por1)
21. The process of claim 5 wherein the metal porphyrin complex is
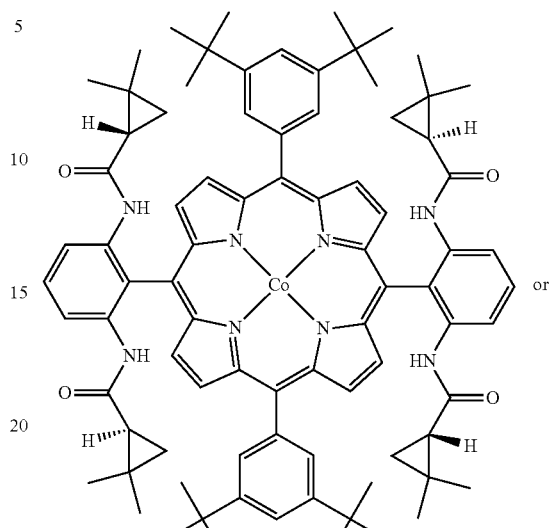
Co(3,5-ditBuChenPhyrin)
or
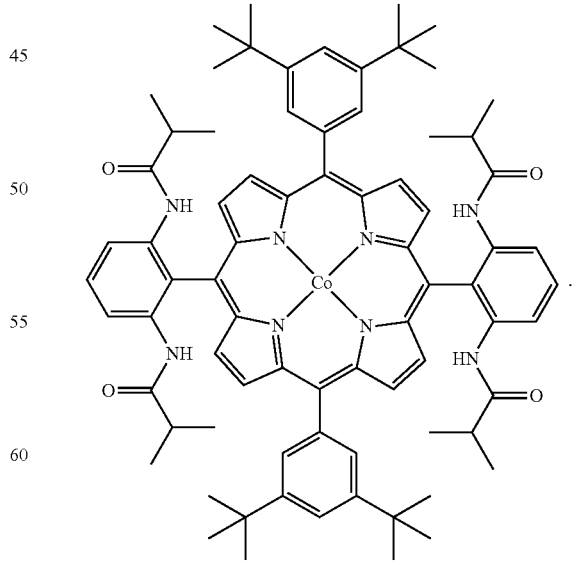
Co(Por1)

22. The process of claim 6 wherein the metal porphyrin complex is
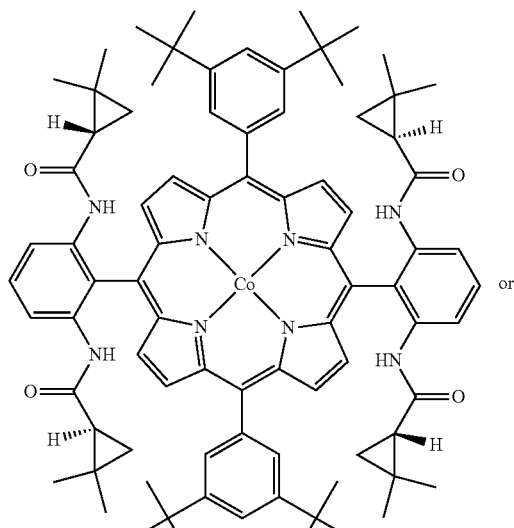
Co(3,5-ditBuChenPhyrin)
or
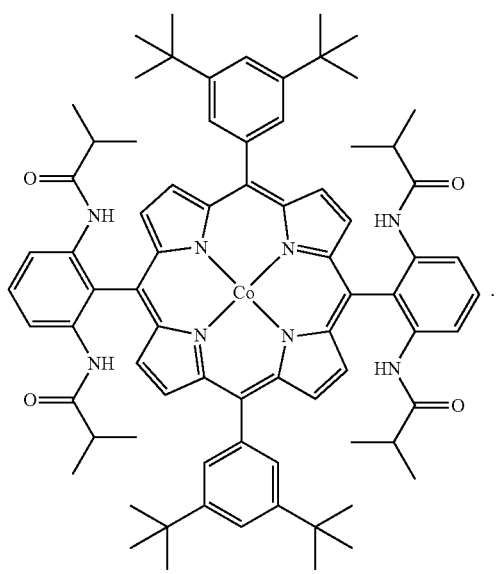
Co(Por1)
23. The process of claim 7 wherein the metal porphyrin complex is
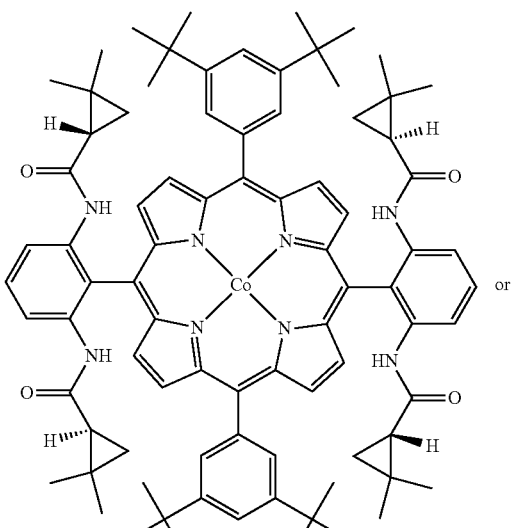
Co(3,5-ditBuChenPhyrin)
or
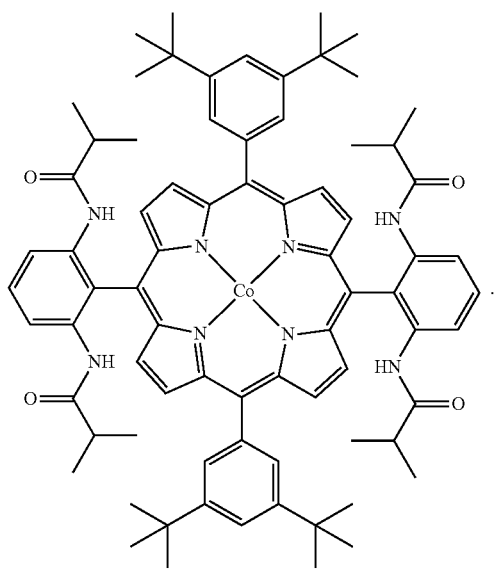
Co(Por1)

24. The process of claim 8 wherein the metal porphyrin complex is
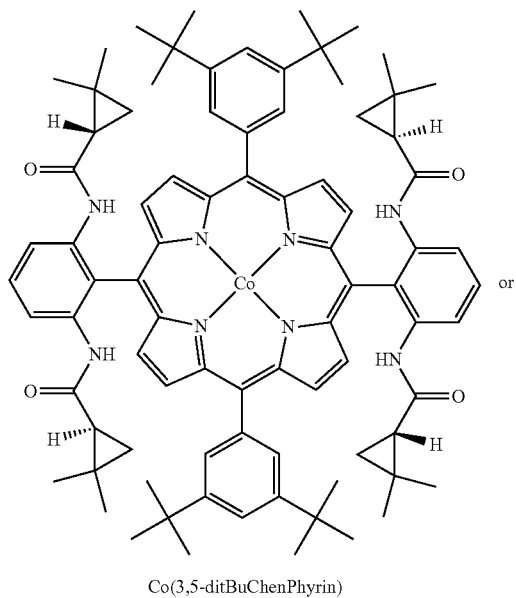
Co(3,5-ditBuChenPhyrin)
or
25. The process of claim 11 wherein the metal porphyrin complex is
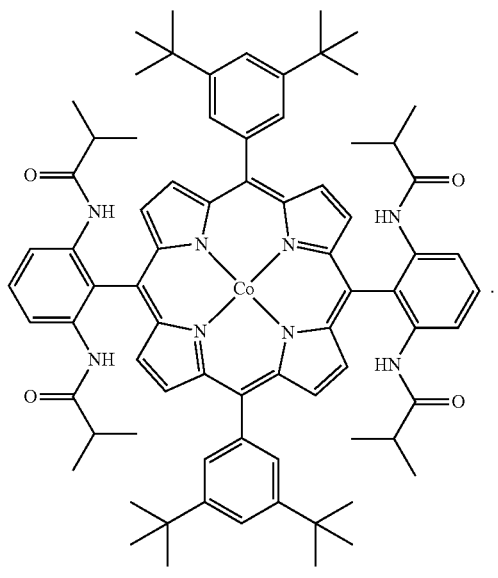
Co(Por1)
26. The process of claim 2 wherein the metal porphyrin complex is
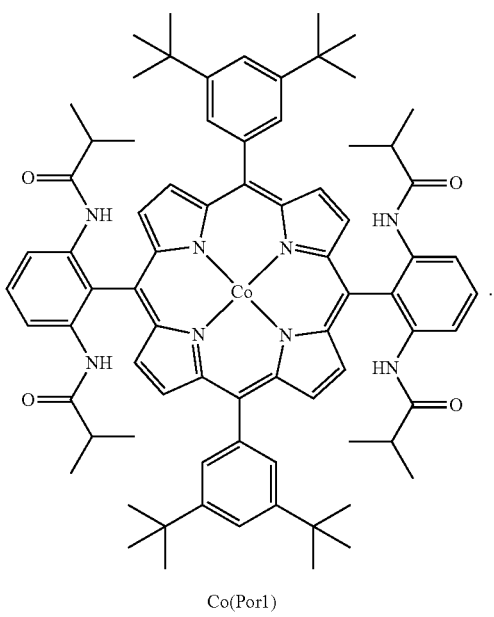
Co(Por1)
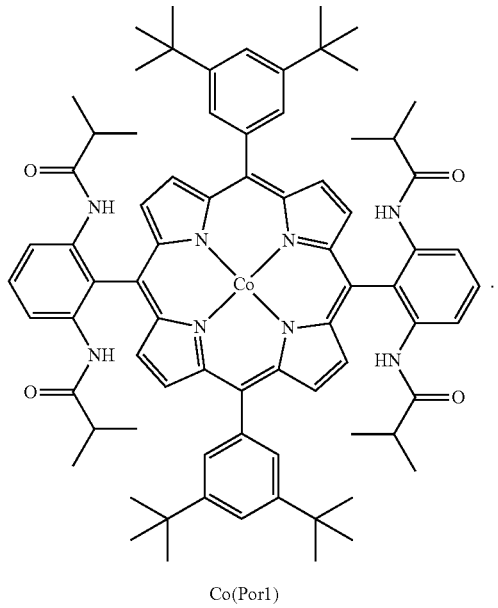
Co(Por1)

27. The process of claim 3 wherein the metal porphyrin complex is
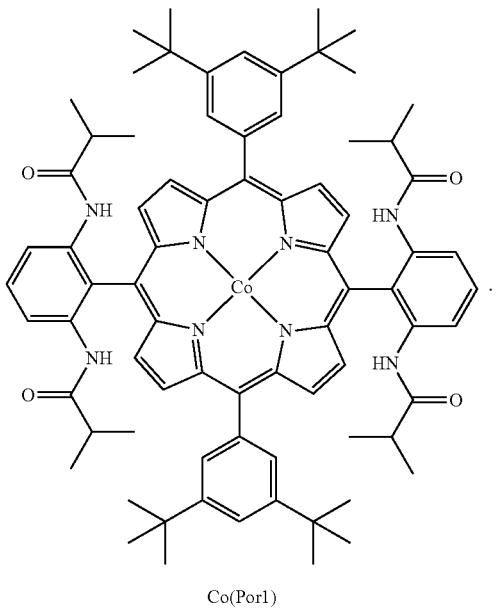
Co(Por1)
28. The process of claim 4 wherein the metal porphyrin complex is
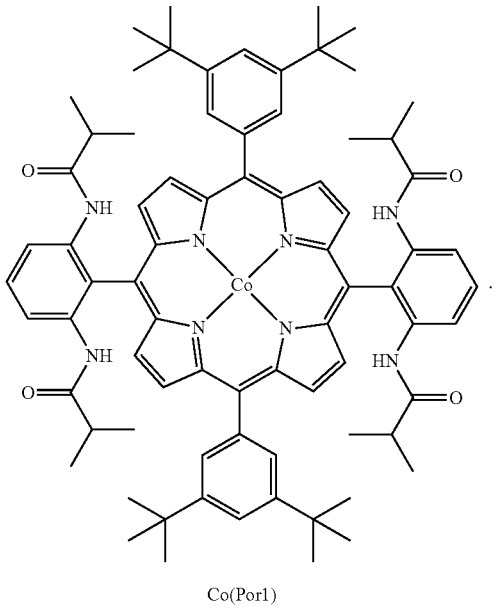
Co(Por1)
29. The process of claim 5 wherein the metal porphyrin complex is
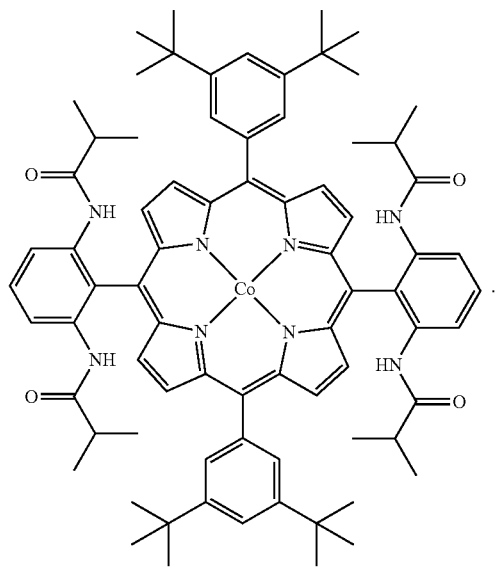
Co(Por1)
30. The process of claim 6 wherein the metal porphyrin complex is
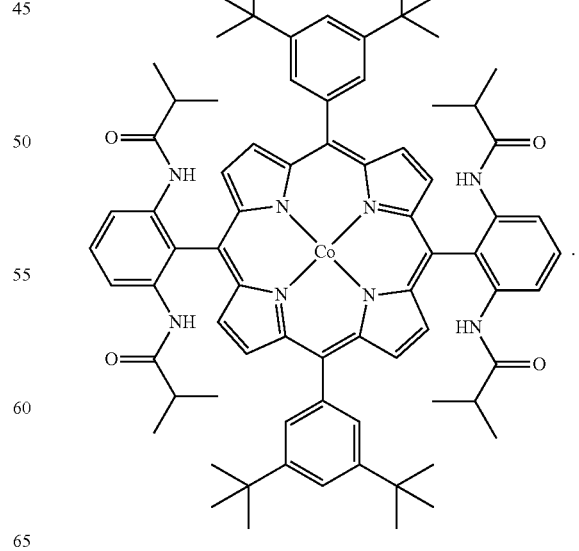
Co(Por1)

31. The process of claim 7 wherein the metal porphyrin complex is
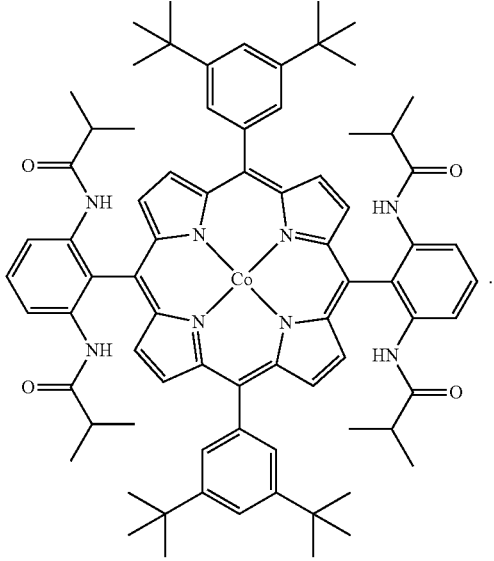
Co(Por1)
32. The process of claim 8 wherein the metal porphyrin complex is
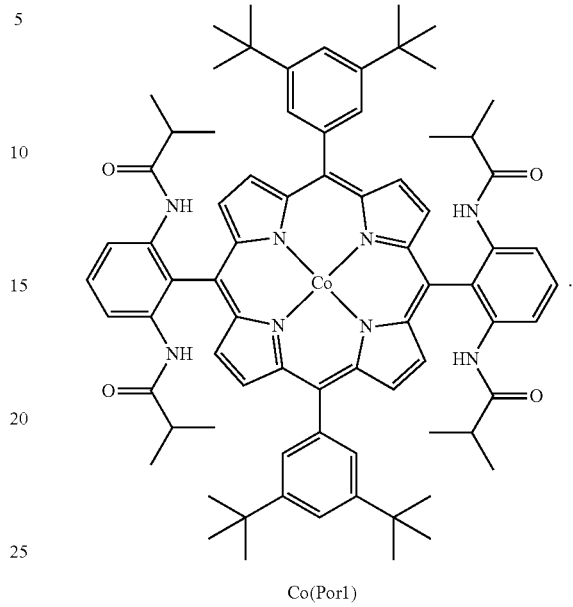
Co(Por1)
* * * * *